(12) United States Patent
Foshee et al.

(10) Patent No.: US 9,636,277 B2
(45) Date of Patent: May 2, 2017

(54) MULTI-CONTAINER FLUID TRANSFER AND DELIVERY DEVICE

(75) Inventors: David L. Foshee, Apex, NC (US); Theodore J. Mosler, Raleigh, NC (US); Nathan R. Snell, Raleigh, NC (US); Matthew R. Penny, Cary, NC (US); Todd M. Korogi, Raleigh, NC (US)

(73) Assignee: YUKON MEDICAL, LLC, Morrisville, NC (US)

( * ) Notice: Subject to any disclaimer, the term of this patent is extended or adjusted under 35 U.S.C. 154(b) by 621 days.

(21) Appl. No.: 13/695,224

(22) PCT Filed: Apr. 29, 2011

(86) PCT No.: PCT/US2011/034676
§ 371 (c)(1),
(2), (4) Date: Oct. 29, 2012

(87) PCT Pub. No.: WO2011/139921
PCT Pub. Date: Nov. 10, 2011

(65) Prior Publication Data
US 2013/0046270 A1 Feb. 21, 2013

Related U.S. Application Data

(60) Provisional application No. 61/329,431, filed on Apr. 29, 2010, provisional application No. 61/435,856, filed on Jan. 25, 2011.

(51) Int. Cl.
*A61B 19/00* (2006.01)
*A61J 1/20* (2006.01)
(Continued)

(52) U.S. Cl.
CPC ........... *A61J 1/2096* (2013.01); *A61J 1/2089* (2013.01); *A61M 5/1782* (2013.01);
(Continued)

(58) Field of Classification Search
CPC ...... A61J 1/2093; A61J 1/2096; A61J 1/2089; A61J 1/2058; A61J 2001/2013; A61J 2001/2017; A61M 5/1782; A61M 5/3129
(Continued)

(56) References Cited

U.S. PATENT DOCUMENTS 4,576,594 A 3/1986 Greenland
4,722,733 A 2/1988 Howson
(Continued)

FOREIGN PATENT DOCUMENTS

JP 11-9656 A 1/1999
JP 2003033424 A 2/2003
(Continued)

OTHER PUBLICATIONS

European Patent Office, European Patent Application No. 11776075.9, Supplemental European Search Report dated Oct. 16, 2014, 6 pages.
(Continued)

*Primary Examiner* — Philip R Wiest
*Assistant Examiner* — Ariana Zimbouski
(74) *Attorney, Agent, or Firm* — Christopher J. Knors; Moore & Van Allen PLLC

(57) ABSTRACT

A multi-container transfer and deliver device and methods of mixing and transferring, the device configured to allow multiple containers to transfer and mix their respective materials and for receiving of the mixed materials to a fluid delivery device. The transfer device comprises a plurality of flow conduits for fluid flow between the multiple containers and the fluid delivery device. A drug mixing kit and optional packaging comprising a multi-container housing with a plurality of flow conduits and a plurality of sections for receiving containers and a fluid transfer device is described.

11 Claims, 28 Drawing Sheets

(51) Int. Cl.
*A61M 5/31* (2006.01)
*A61M 5/178* (2006.01)

(52) U.S. Cl.
CPC ............ *A61M 5/3129* (2013.01); *A61J 1/201* (2015.05); *A61J 1/2017* (2015.05); *A61J 1/2037* (2015.05); *A61J 1/2058* (2015.05); *A61J 1/2075* (2015.05); *A61J 1/2082* (2015.05)

(58) Field of Classification Search
USPC .................................................. 604/407, 415
See application file for complete search history.

(56) References Cited

U.S. PATENT DOCUMENTS

| | | |
|---|---|---|
| 5,304,165 A | 4/1994 | Haber |
| 5,329,976 A | 7/1994 | Haber et al. |
| 6,364,865 B1 | 4/2002 | Lavi et al. |
| 6,475,183 B1 | 11/2002 | Epstein et al. |
| 6,478,771 B1 | 11/2002 | Lavi et al. |
| 6,488,650 B1 | 12/2002 | Epstein et al. |
| 6,575,205 B2 | 6/2003 | Epstein et al. |
| 6,641,565 B1 | 11/2003 | Lavi et al. |
| 6,645,181 B1 | 11/2003 | Lavi et al. |
| 6,689,108 B2 | 2/2004 | Lavi et al. |
| 6,689,966 B2 | 2/2004 | Wiebe |
| 6,719,719 B2 | 4/2004 | Carmel et al. |
| 6,723,068 B2 | 4/2004 | Lavi et al. |
| 6,779,566 B2 | 8/2004 | Engel |
| 7,081,103 B2 | 7/2006 | Epstein et al. |
| 7,083,043 B2 | 8/2006 | Sharon |
| 7,207,969 B2 | 4/2007 | Epstein et al. |
| 7,523,822 B2 | 4/2009 | Sharon |
| 7,540,863 B2 | 6/2009 | Haindl |
| 7,862,538 B2 | 1/2011 | Sawhney et al. |
| 2002/0004643 A1 | 1/2002 | Carmel et al. |
| 2002/0007671 A1 | 1/2002 | Lavi et al. |
| 2002/0021284 A1 | 2/2002 | Wiebe |
| 2002/0087118 A1 | 7/2002 | Reynolds et al. |
| 2002/0123719 A1 | 9/2002 | Lavi et al. |
| 2003/0023203 A1 | 1/2003 | Lavi et al. |
| 2003/0024830 A1 | 2/2003 | Sharon |
| 2004/0015134 A1 | 1/2004 | Lavi et al. |
| 2004/0030285 A1 | 2/2004 | Lavi et al. |
| 2004/0069044 A1 | 4/2004 | Lavi et al. |
| 2006/0149189 A1* | 7/2006 | Diamond et al. ............. 604/118 |
| 2007/0088315 A1 | 4/2007 | Haindl |
| 2007/0156118 A1* | 7/2007 | Ramsey et al. ............... 604/533 |
| 2009/0099547 A1 | 4/2009 | Radmer |
| 2010/0084041 A1 | 4/2010 | Fehr et al. |
| 2012/0029464 A1* | 2/2012 | Kragelund et al. ........... 604/414 |
| 2012/0330228 A1 | 12/2012 | Day et al. |

FOREIGN PATENT DOCUMENTS

| | | |
|---|---|---|
| JP | 2003527933 A | 9/2003 |
| JP | 2004529739 A | 9/2004 |
| JP | 2006174988 A | 7/2006 |
| WO | 9110417 A1 | 7/1991 |
| WO | WO02/102295 A2 | 12/2002 |
| WO | WO/2007/101798 A2 | 9/2007 |
| WO | WO2007122209 | 11/2007 |
| WO | WO2009026443 | 2/2009 |
| WO | WO2010043685 * | 4/2010 |
| WO | 2010141632 A2 | 12/2010 |

OTHER PUBLICATIONS

Japanese Patent Office; Japanese Patent Application No. 2012-514102 Office Action dated Mar. 14, 2012, pp. 1-8.
Korean Intellectual Property Office, PCT International Search Report for International Application No. PCT/US2011/034676 date of completion Jan. 27, 2012.
Korean Intellectual Property Office, PCT International Preliminary Report on Patentability and Written Opinion of the International Searching Authority for International Application No. PCT/US2011/034676 date of issuance Oct. 30, 2012.
European Patent Office, European Patent Application No. 10784039.9, Supplemental European Search Report dated Oct. 16, 2014, 6 pages.
Yukon Medical, LLC, et al., International Search Report and Written Opinion for International Application No. PCT/US2010/037133 dated Feb. 22, 2011, 9 pages.
Yukon Medical, LLC, et al., International Preliminary Report of Patentability for International Application No. PCT/US2010/037133 dated Dec. 15, 2011, 6 pages.
Yukon Medical, LLC, USPTO Non-Final Office Action for U.S. Appl. No. 13/375,990 dated Nov. 10, 2014, 24 pages.
Yukon Medical, LLC, USPTO Final Office Action for U.S. Appl. No. 13/375,990 dated Jun. 5, 2015, 11 pages.
European Patent Office; Office Action for European Patent Application No. 10784039.9 dated Oct. 30, 2015, 5 Pages.
USPTO; Corrected Notice of Allowability for U.S. Appl. No. 13/375,990 dated Dec. 3, 2015, 6 Pages.

* cited by examiner

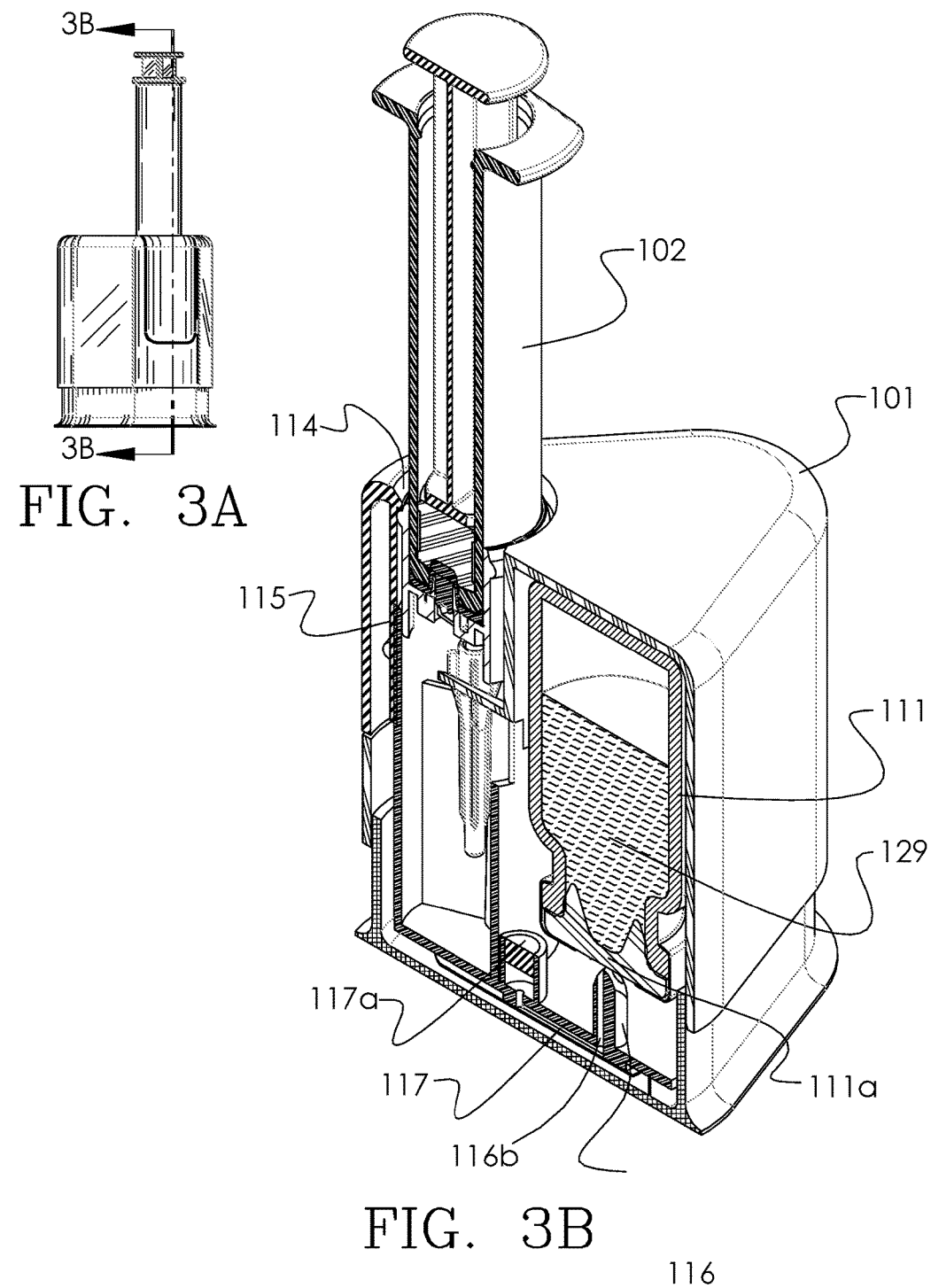

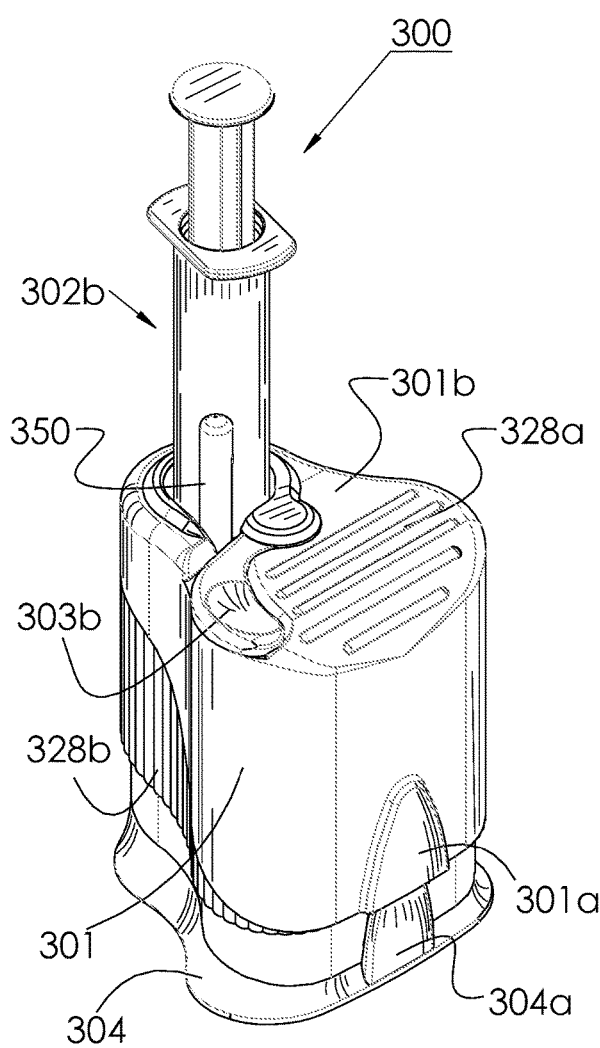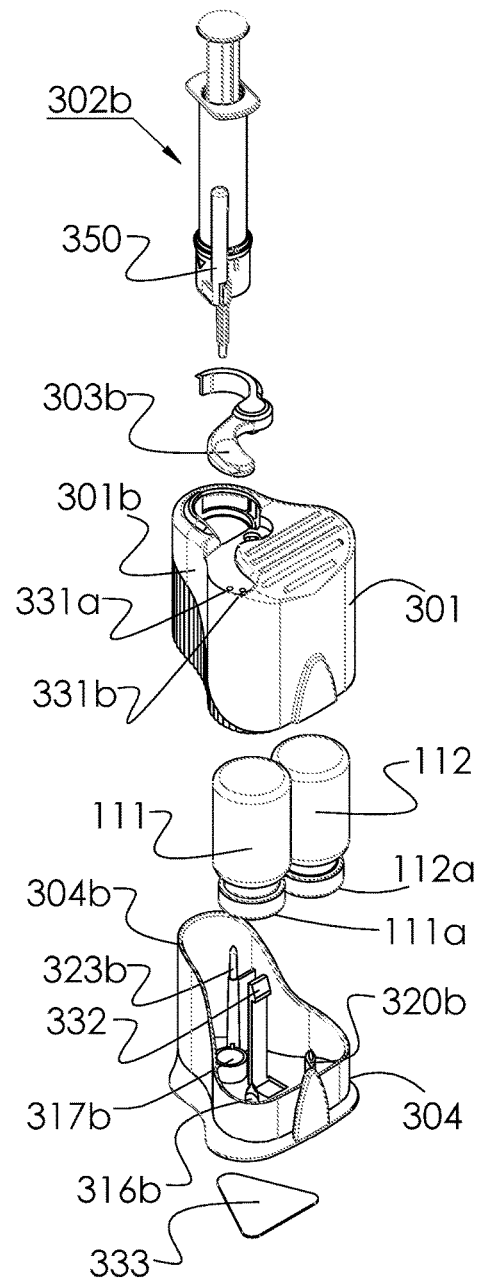
FIG. 11A
FIG. 11B

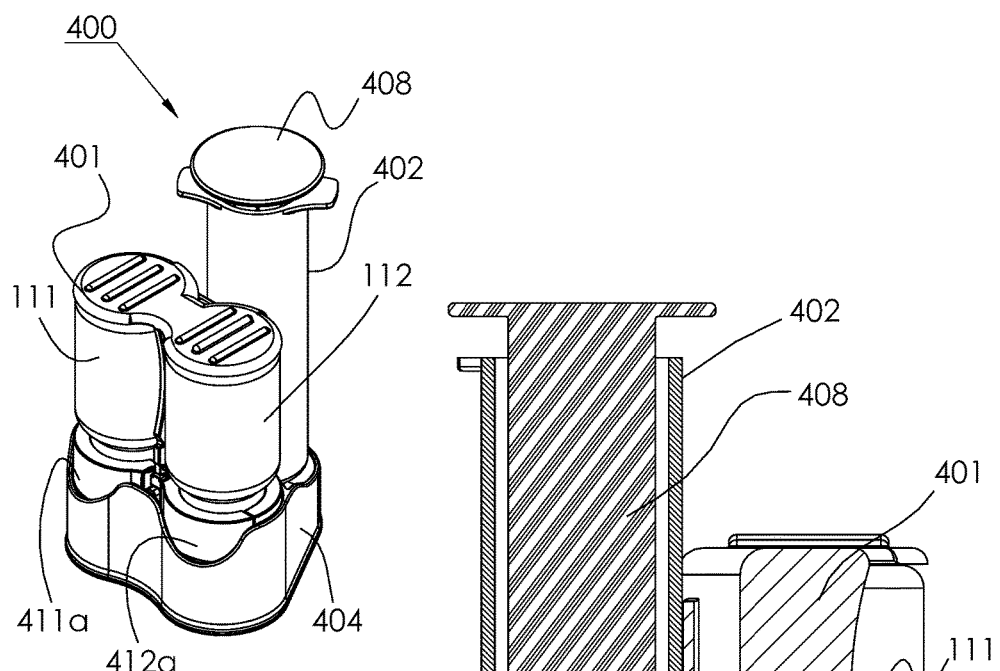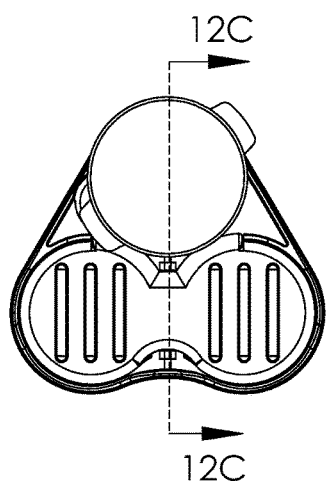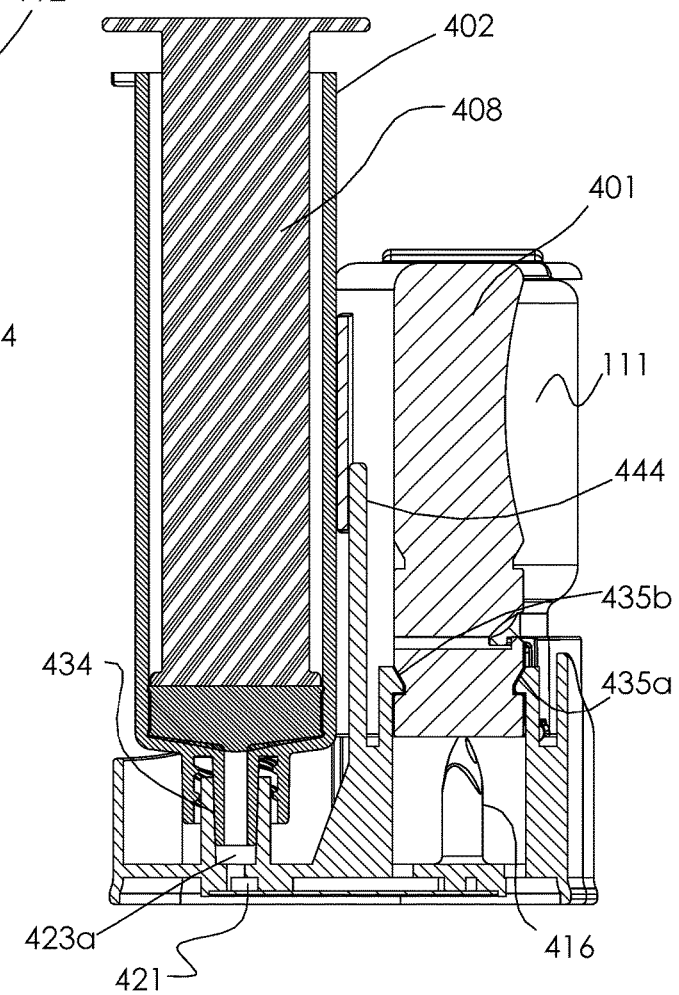
FIG. 12A
FIG. 12B
FIG. 12C

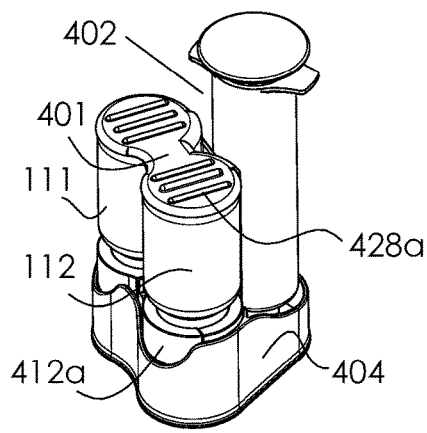
FIG. 13A
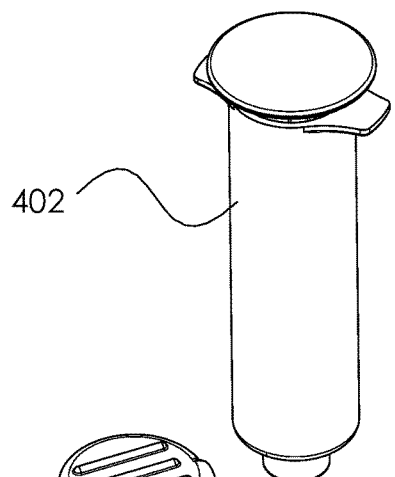
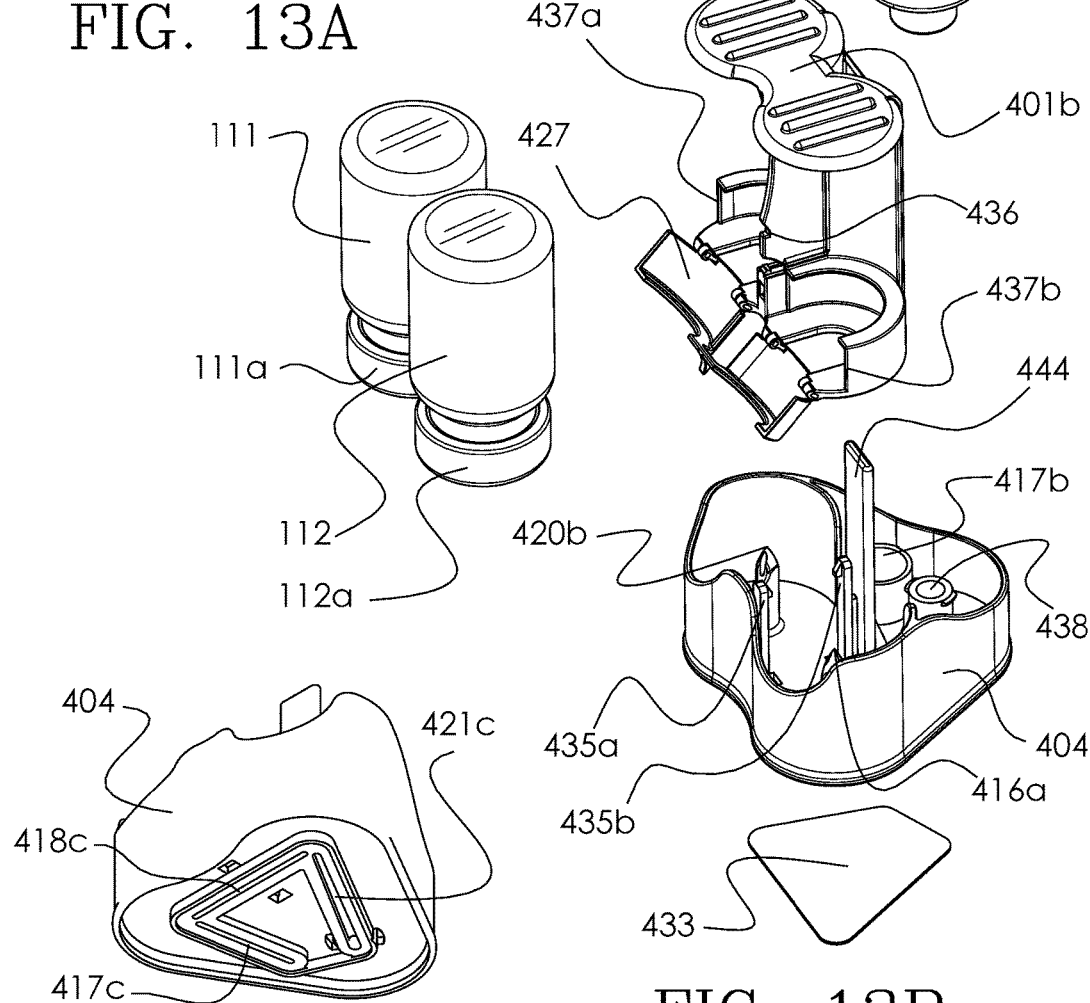
FIG. 13B
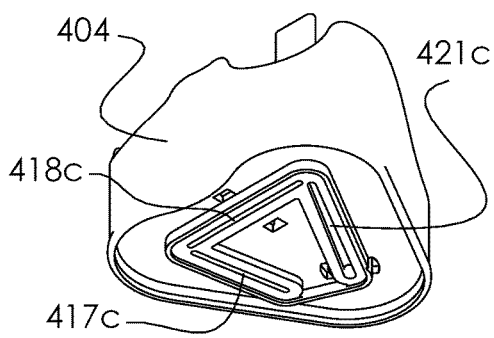
FIG. 13C

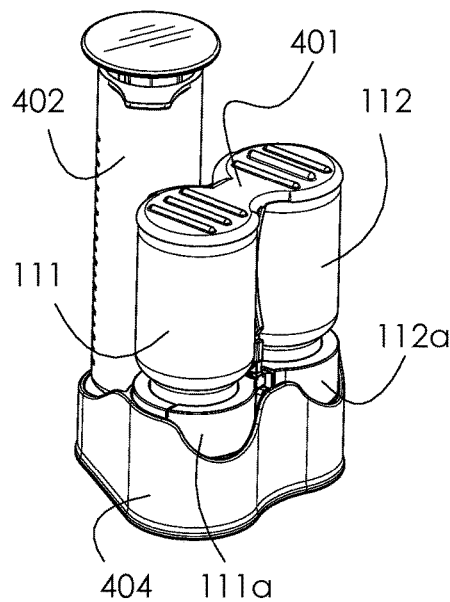
FIG. 14A
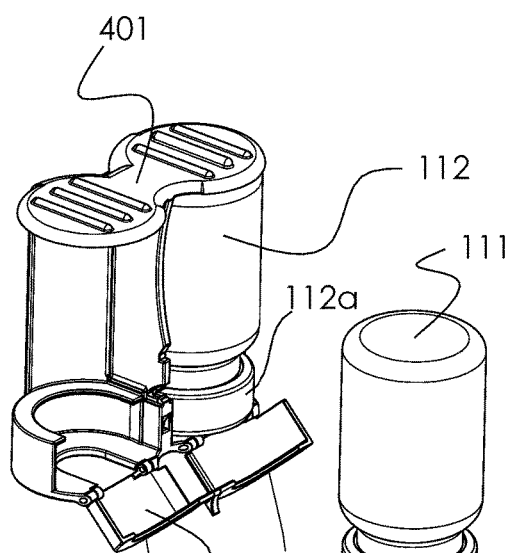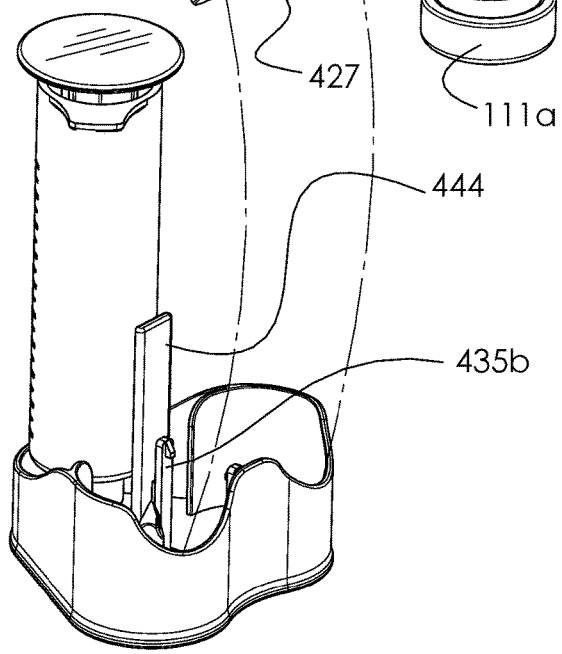
FIG. 14B

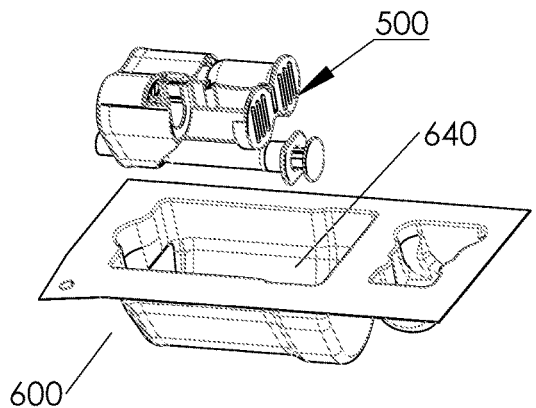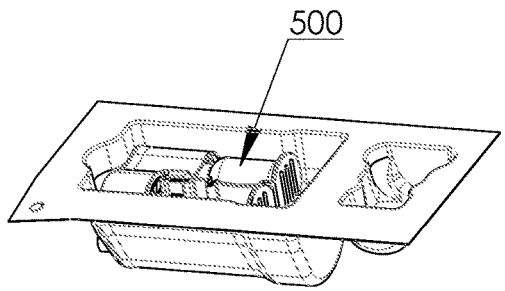
FIG. 17A    FIG. 17B
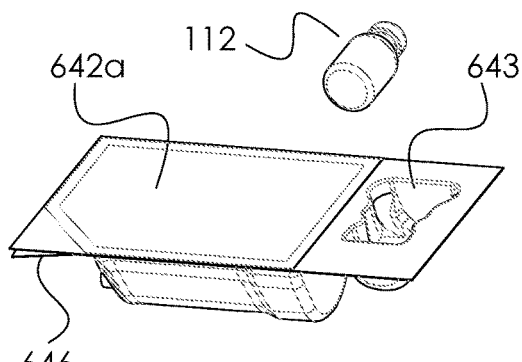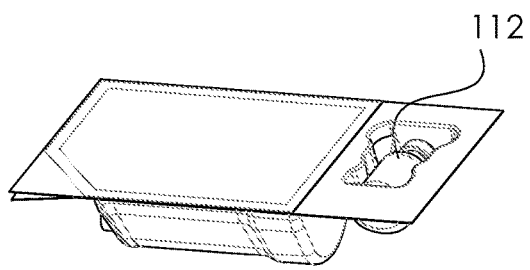
FIG. 17C    FIG. 17D
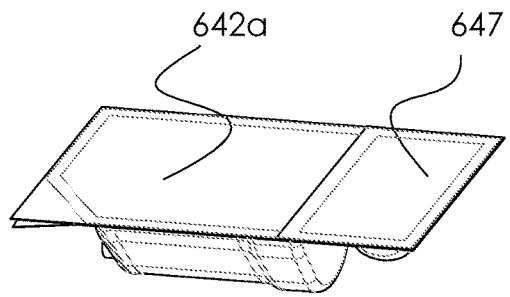
FIG. 17E

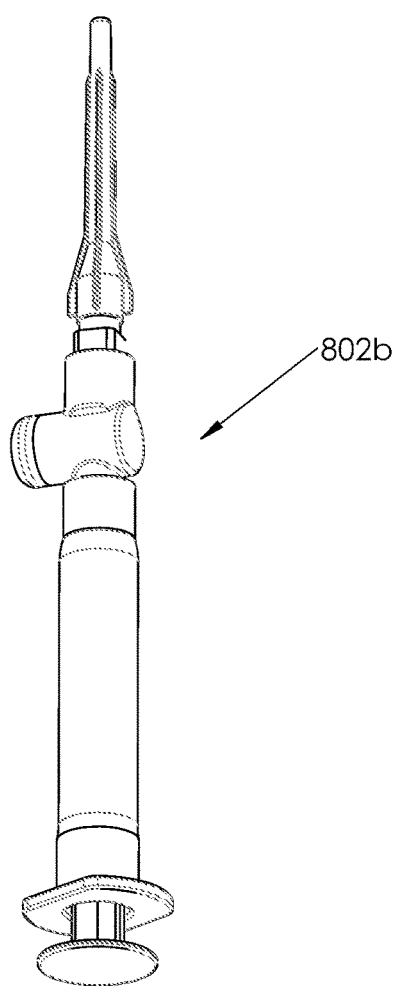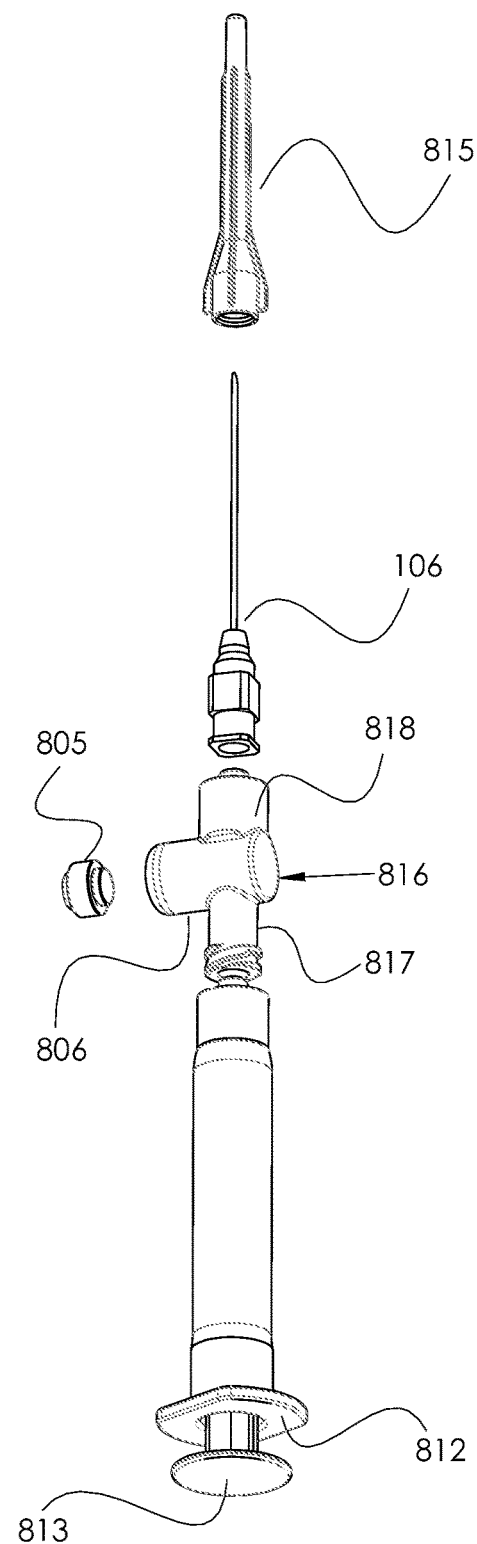
FIG. 24A
FIG. 24B

MULTI-CONTAINER FLUID TRANSFER AND DELIVERY DEVICE

CROSS-REFERENCE TO RELATED APPLICATIONS

This application is filed under the provisions of 35 U.S.C. §371 and claims the benefit of International Patent Application No. PCT/US2011/034676, filed on Apr. 29, 2011, entitled "MULTI-CONTAINER FLUID TRANSFER AND DELIVERY DEVICE", which claims the benefit of U.S. Provisional Application No. 61/435,856, filed on Jan. 25, 2011 and U.S. Provisional Application No. 61/329,431, filed on Apr. 29, 2010, each of which is hereby incorporated by reference herein in its entirety.

TECHNICAL FIELD

A multi-container transfer and delivery device configured to allow multiple containers to transfer and mix their respective materials and for receiving of the mixed materials to a delivery device. The transfer device comprises a plurality of flow conduits for fluid flow between the multiple containers and the delivery device. Methods of mixing using the device and methods of sterilizing the device are described. A drug mixing kit comprising a multi-container housing with a plurality of flow conduits and a plurality of compartments for receiving containers and a transfer device is also described.

BACKGROUND

Lyophilized and similar liquid drugs are typically provided in medicament vials with standard elastomeric closure sizes, such as 20 mm and 13 mm diameter closures. Injections of these drugs, if administered to patients intramuscularly, intravenously, subcutaneously, and the like, require syringes with needles for delivery to the patient. Needles used to administer a drug to a patient are often different from the needle or access device used to access the medicament vials. Certain needle types are special for drug vials—such as anti-coring needles—and would be inappropriate for use when injecting a patient. For instance, a pharmacy technician may use a high flow rate needle to withdraw diluent from one source, and inject it into a lyophilized drug vial. The drug is then mixed accordingly and drawn back into the syringe—or perhaps a new, sterile syringe. Oftentimes the drug preparation needle is removed, disposed of and replaced by an alternate sterile needle appropriate for the specific type of patient injection e.g. deltoid intramuscular. Because prescribed mixing and preparation of drugs vary, certain drugs need to be mixed carefully, or flow through specific sized needles; or the drug is extremely expensive so residual drug left in the vial is undesirable. This is difficult to resolve due, in part, to vial closure design and varying materials. So it may become important to pair the appropriate needle or access device with the medicament vial. Furthermore, the resultant injection process varies—the location and type of injection. Someone other than the prescriber, typically a technician or nurse, often completes the preparation and may not even be the administrator of the medication. So, there are multiple steps that can be done in error. The time of preparation can be significant, adding cost and complexity to the process. By switching needles so often and using them for drug preparation, the likelihood of needle-stick injuries increases, causing pain and concern for healthcare providers, at a minimum, and leading to potential transmission of blood borne pathogens and potentially serious diseases. The necessary aseptic preparation of a drug and its delivery is also a challenge to the caregiver and presents a safety concern for the patient if not performed well.

SUMMARY

Disclosed and described herein is a multi-container transfer and delivery device capable of addressing several of the issues described above. The disclosed device reduces the number of steps and potential errors for preparation and administration of drugs, safeguards end-users and others from accidental needle-sticks, provides for high flow conduits to expedite preparation and to protect the drug and/or blood products from mechanical/shearing forces thus preventing or eliminating drug breakdown or hemolysis. This results in drug preparation and delivery that is simplified, efficient, and effective.

In a first embodiment, a transfer device is provided. The device comprises a base plate, an upper housing, and a lower housing securable to the base plate, the lower housing slidably receiving a portion of the upper housing; wherein the lower housing provides multiple compartments configured for receiving at least two containers, each having a pierceable portion associated therewith, and one of the multiple compartments configured to receive a horizontally presented delivery device. A fluidic conduit system is integral with the lower housing providing fluid communication between at least two of the multiple compartments.

In a first aspect of the first embodiment, the fluidic conduit system comprises: (i) a vent and optionally, a check valve; (ii) a first container accessing member having a longitudinal axis distally projecting essentially vertical from the lower housing, and having corresponding therewith a first fluid lumen and a second fluid lumen essentially parallel with the longitudinal axis, the first fluid lumen of the first container accessing member in fluid communication with the vent; (iii) a second container accessing member having a longitudinal axis distally projecting essentially vertical from the lower housing, and having corresponding therewith a first fluid lumen and a second fluid lumen essentially parallel with the longitudinal axis, the first fluid lumen of the second container accessing member in fluid communication with the second fluid lumen of the first container accessing member; and (iv) a delivery device accessing member having a longitudinal axis distally projecting essentially vertical from the lower housing, and having corresponding therewith a first fluid lumen essentially parallel with the longitudinal axis, the first fluid lumen of the delivery device accessing member in fluid communication with the second fluid lumen of the second container accessing member.

In a second aspect, alone or in combination with the previous aspect of the first embodiment, the delivery device accessing member further comprises a fluid flow controller.

In a third aspect, alone or in combination with any one of the previous aspects of the first embodiment, the fluid flow controller comprises a collapsible elastomeric sleeve having a first state fluidically sealing the first fluid lumen of the delivery device access member, and a second state providing fluid communication between a delivery device and the fluidic conduit system.

In a fourth aspect, alone or in combination with any one of the previous aspects of the first embodiment, the lower housing comprises (i) a first flow channel fluidically communicating the first fluid lumen of the first container accessing member with the vent; (ii) a second flow channel fluidically communicating the first fluid lumen of the second container accessing member with the second fluid lumen of the first container accessing member, and (iii) a third flow channel fluidically communicating the first fluid lumen of the delivery device accessing member with the second fluid lumen of the second container accessing member; wherein the flow channels (i)-(iii) are physically isolated from each other and form at least a portion of the fluidic conduit system by combination of the base plate and the lower housing.

In a fifth aspect, alone or in combination with any one of the previous aspects of the first embodiment, each of the longitudinal axes of the first container accessing member, the second container accessing member, and the delivery device accessing member distally project in the same direction relative to the lower housing.

In a sixth aspect, alone or in combination with any one of the previous aspects of the first embodiment, the device further comprises a first container comprising a liquid, the first container operably positioned with first container accessing member.

In a seventh aspect, alone or in combination with any one of the previous aspects of the first embodiment, the device further comprises a second container comprising a medicament, the second container operably positioned with second container accessing member.

In an eighth aspect, alone or in combination with any one of the previous aspects of the first embodiment, the device further comprises a second container comprising a medicament, the second container operably positioned with second container accessing member.

In a ninth aspect, alone or in combination with any one of the previous aspects of the first embodiment, the device further comprises a syringe operably positioned with the delivery device accessing member, the syringe comprising an adapter having a first end for receiving the syringe; a second end for receiving a dispensing member; and an adapter housing comprising a pierceable fluid by-pass element accessible by the delivery device accessing member of the transfer device.

In a second embodiment a transfer device is provided. The device comprises a base plate, an upper housing, and a lower housing securable to the base plate and providing multiple compartments, the lower housing slidably receiving a portion of the upper housing, a fluidic conduit system integral with the lower housing providing fluid communication between the multiple compartments, the fluidic conduit system comprising: (i) a first container accessing member having a longitudinal axis distally projecting essentially vertical from the lower housing, and having corresponding therewith a first fluid lumen and a second fluid lumen essentially parallel with the longitudinal axis, the first fluid lumen of the first container accessing member in fluid communication with the vent; (ii) a second container accessing member having a longitudinal axis distally projecting essentially vertical from the lower housing, and having corresponding therewith a first fluid lumen and a second fluid lumen essentially parallel with the longitudinal axis, the first fluid lumen of the second container accessing member in fluid communication with the second fluid lumen of the first container accessing member; and (iii) a delivery device accessing member configured to control fluid communication between a delivery device and the fluidic conduit system, the delivery device accessing member having a first fluid lumen in fluid communication with the second fluid lumen of the second container accessing member.

In a first aspect of the second embodiment, the delivery device accessing member is configured with at least one of the following: (a) a valved access connector; and (b) a pierceable septum.

In a second aspect, alone or in combination with the previous aspect of the second embodiment, the lower housing comprises: (i) a first flow channel fluidically communicating the first fluid lumen of the first container accessing member with a vent and/or optional check valve; (ii) a second flow channel fluidically communicating the first fluid lumen of the second container accessing member with the second fluid lumen of the first container accessing member, and (iii) a third flow channel fluidically communicating the first fluid lumen of the delivery device accessing member with the second fluid lumen of the second container accessing member; the flow channels (i)-(iii) being physically isolated from each other and forming at least a portion of the fluidic conduit system by combination of the base plate and the lower housing.

In a third aspect, alone or in combination with any one of the previous aspects of the second embodiment, the device further comprises a check valve in fluid communication with the first flow channel.

In a fourth aspect, alone or in combination with any one of the previous aspects of the second embodiment, the valved access connector is a female valved connector or collapsible elastomeric sleeve.

In a fifth aspect, alone or in combination with any one of the previous aspects of the second embodiment, he pierceable septum is configured for receiving a valved male luer.

In a sixth aspect, alone or in combination with any one of the previous aspects of the second embodiment, each of the longitudinal axes of the first container accessing member, the second container accessing member, and the delivery device accessing member distally project in the same direction relative to the lower housing.

In a seventh aspect, alone or in combination with any one of the previous aspects of the second embodiment, the device further comprises a first container comprising a liquid, the first container operably positioned with first container accessing member.

In an eighth aspect, alone or in combination with any one of the previous aspects of the second embodiment, the device further comprises a second container comprising a medicament, the second container operably positioned with second container accessing member.

In a ninth aspect, alone or in combination with any one of the previous aspects of the second embodiment, the device further comprises a syringe configured to operably couple with the delivery device accessing member.

In a tenth aspect, alone or in combination with any one of the previous aspects of the second embodiment, the syringe comprises a distal end having a collapsible elastomeric sleeve, the sleeve having a first state fluidically sealing the distal end of the syringe, and a second state operably coupled to the delivery device accessing member so as to provide fluid communication between the syringe and the fluidic conduit system.

In a third embodiment, an adapter is provided. The adapter comprising a first end for receiving a syringe, the first end having a first conduit, a second end for receiving a dispensing member, the second end having a second conduit, and an adapter housing positioned between the first end and the second end and in fluidic communication therewith, the adapter housing having an opening sealed with elastomeric septum.

In a first aspect of the third embodiment, the elastomeric septum in a first state provides fluidic communication between the adapter housing, the first conduit and the second conduit of the adapter, and in a second state, upon coupling with a transfer device of any of the above embodiments, prevents fluidic communication the between the second conduit and adapter housing.

In a second aspect, alone or in combination with the previous aspect of the third embodiment, the elastomeric septum is a split-septum.

In a third aspect, alone or in combination with the previous aspect of the third embodiment, the adapter further comprises a one-way flow control valve.

In a fourth aspect, alone or in combination with the previous aspect of the third embodiment, the elastomeric septum is configured for coupling with the delivery device accessing member of the transfer device as defined in of any one of first or second embodiments.

In a fourth embodiment, a syringe is provided comprising the adapter of the third embodiment.

In a fifth embodiment, a kit is provided. The kit comprises: (i) a transfer device as defined in of any one of the previous first or second embodiments, at least one of (i) an adapter as defined in the third embodiment; and (ii) a syringe as defined in the fourth embodiment; (ii) a first container adapted for receipt by the transfer device, the first container comprising a fluid, and (iii) optionally, a packaging member.

In a first aspect of the fifth embodiment, the adapter is integral with the syringe.

In a second aspect, alone or in combination with the previous aspect of the fifth embodiment, the kit further comprises a dispensing member cover and/or needle safety device.

In a third aspect, alone or in combination with the previous aspect of the fifth embodiment, the packaging member comprising a first receptacle configured to receive the transfer device and the first container; and a lid sealable across the first receptacle.

In a fourth aspect, alone or in combination with the previous aspect of the fifth embodiment, the transfer device and the first container are operably assembled for use.

In a fifth aspect, alone or in combination with the previous aspect of the fifth embodiment, the kit further comprises a second container.

In a sixth embodiment, a method of mixing and transferring is provided. The method comprising providing a device of any one of the first or second embodiments.

In a seventh aspect, alone or in combination with the previous aspect of the fifth embodiment, the packaging member is configured to separately receive the second container in a second receptacle.

In an eighth aspect, alone or in combination with the previous aspect of the fifth embodiment, the transfer device and the second container are operably assembled for use.

In a sixth embodiment, a method of mixing and transferring is provided. The method comprising providing a device as defined the first or second embodiments; and optionally providing at least one container having a pierceable opening.

In a first aspect of the ninth embodiment, the method further comprises introducing the at least two containers to the lower housing of the device such that their pierceable openings are operably configured with the corresponding container accessing members, and sequentially or concurrently, operably coupling a syringe to the delivery device accessing member.

In a second aspect, alone or in combination with the previous aspect of the ninth embodiment, the method further comprises urging the upper housing towards the lower housing so that the containers are accessed by the corresponding container accessing members through their pierceable openings.

In a third aspect, alone or in combination with the previous aspect of the ninth embodiment, the method further comprises sequentially or concurrently, transferring at least a portion of the contents from the at least two containers into the syringe.

BRIEF DESCRIPTION OF THE DRAWINGS

FIGS. 3A-3B are section plane and corresponding cross-sectional views of the transfer and delivery device of FIG. 1 in an initial state, as disclosed and described herein.

FIGS. 11A-11B are a perspective view and exploded view of an alternative embodiment of the device, as disclosed and described herein.

FIGS. 12A-12C are an orthogonal, top and section view, respectively, of an alternative embodiment of a transfer and delivery device, as disclosed and described herein.

FIGS. 13A-13C are perspective views and an exploded view of an alternative embodiment of a transfer and delivery device, as disclosed and described herein.

FIGS. 14A-14B are perspective views of an aspect of an alternative embodiment of a transfer and delivery device, as disclosed and described herein.

FIGS. 17A-17E are perspective views of a packaging system for the transfer and delivery device as disclosed and described herein.

FIGS. 24A and 24B are a perspective view and exploded view, respectively, of a syringe and removable adapter as disclosed and described herein.

DETAILED DESCRIPTION

Figure 1:
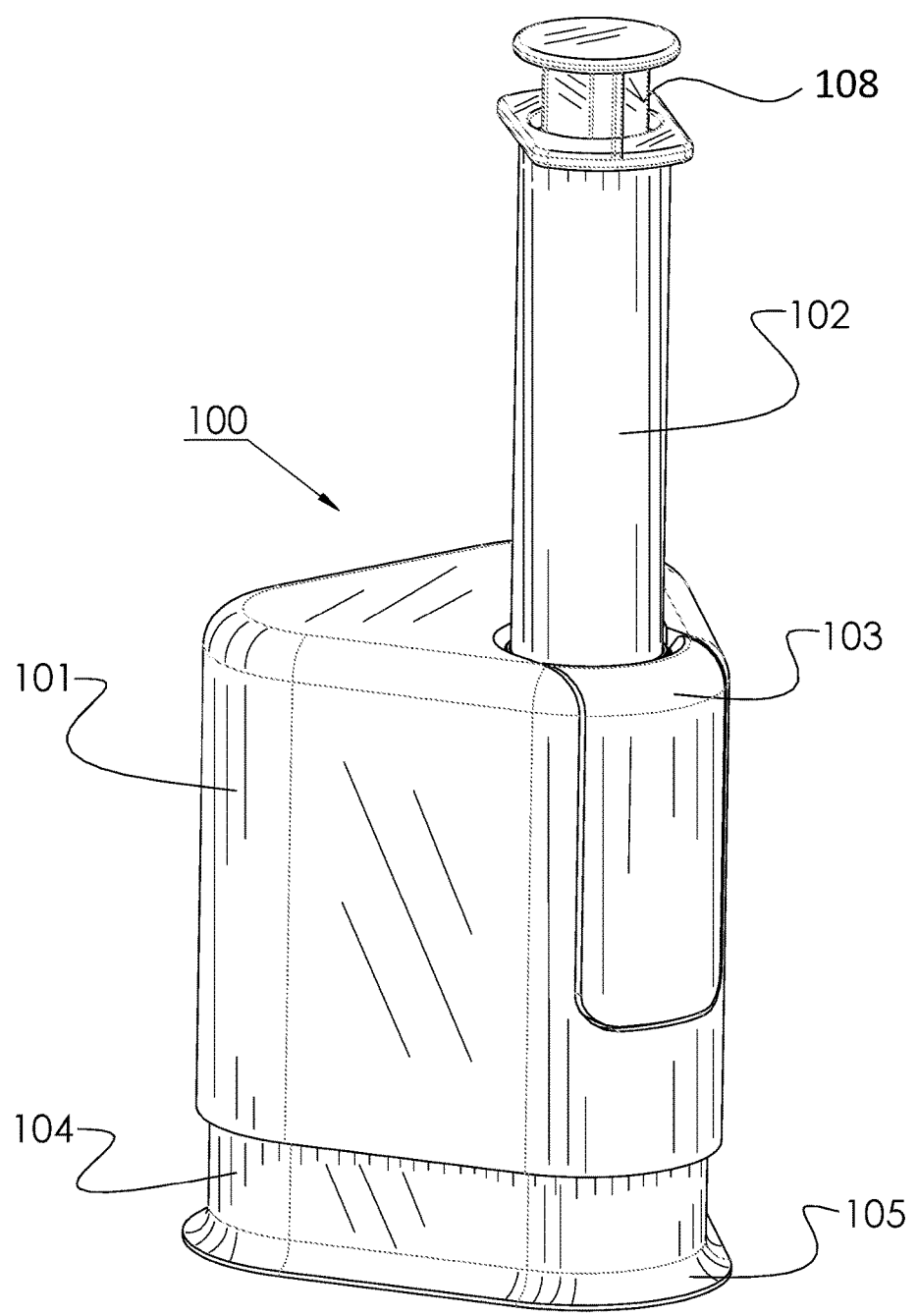
FIG. 1 is a perspective view of a transfer and delivery device as disclosed and described herein.

Throughout the specification, the term "fluid" as used herein is inclusive of gaseous, liquid, and combinations of gas and liquid medium unless specifically designated as limited to a particular medium.

Throughout the specification, the term "media" as used herein is inclusive of fluids and solid form mediums unless specifically designated as limited to a particular medium. In one aspect the media is diluent or liquid. In another aspect, the media is a medicament, which can be a pharmaceutical or biologic agent. The form of the medicament is not limited, and can be, for example, a solid, powder, liquid, dispersion, suspension, emulsion, gel, or combination thereof.

Throughout the specification, the phrases "first container" and "first media container" are used interchangeably. This container is also referred to as a "vial" unless otherwise stated, without any express or implied limitation to the scope of any claim, and are inclusive of any device with similar functionality to that of a vial, but not necessarily the structure of a vial.

Throughout the specification, the phrases "second container" and "intermediate media container" are used interchangeably. This container is also referred to as a "vial" unless otherwise stated, without any express or implied limitation to the scope of any claim, and are inclusive of any device with similar functionality to that of a vial, but not necessarily the structure of a vial.

Throughout the specification, the term "liquid" as used herein is inclusive of suspensions, oil-in-water emulsions, water-in-oil emulsions, and liquids with or without dissolved, dispersed, or contained solids irrespective of the size of the solids or the amount present.

Throughout the specification, the phrases "dual vial access device," "drug reconstitution device," "transfer and delivery device" and "fluid transfer and delivery device" are used interchangeably, unless otherwise stated, without any express or implied limitation to the scope of any claim. As is understood by one having ordinary skill in the art, a fluid transfer and delivery device provides for introduction of fluid from one container to another, while a fluid control device may include flow control means for diverting, metering, or interrupting flow between at least two flow paths.

Throughout the specification, the phrases "fluid delivery container", "final media container" "delivery device", and the term "syringe" are used interchangeably unless otherwise stated, without any express or implied limitation to the scope of any claim, and are inclusive of any device with similar functionality to that of a syringe, but not necessarily the structure of a syringe.

Throughout the specification, the phrase "biologic drug" is inclusive of any substance that is made from a living organism or its products and is used in the prevention, diagnosis, or treatment of diseases. Biologic drugs include, without limitation, antibodies, interleukins, antibiotics, and vaccines. The phrase "biologic drug" is also known as, and is herein inclusive of "biologics", "biologic agent" and "biological agent."

The fluid transfer and delivery device for the transfer of fluids between containers herein disclosed and described can be configured in a variety of ways. The device may be used in connection with the transfer of a fluid into a container in which there is a vacuum. Any piercing members are designed to penetrate elastomeric septums, sealing the containers.

In various embodiments of the present disclosure, a transfer system is provided in which the transfer system includes a transfer device configured to receive and mix contents of containers and allow the transfer of the mixture to a fluid delivery container having a needle/cannula or needle safety device, thus avoiding subsequent needle/cannula attachment after media transfer and/or requiring removal of a needle cover or activating a syringe safety system before or after media transfer. The system comprises a base plate, an upper housing and a lower housing securable to the base, the lower housing slidably receiving a portion of the upper housing; providing for multiple compartments, at least two of the multiple compartments associated with the portion of the upper housing and configured for receiving at least two containers, each having a pierceable portion associated therewith, and one of the multiple compartments configured to receive a delivery device oriented either parallel or horizontal to the base of the device; and a fluidic conduit system integral with the base providing fluid communication between the three compartments. In certain aspects, it is advantageous to provide a transfer device that receives the delivery device (e.g., syringe) in a horizontal presentation. For example, in a horizontal configuration, syringes can be provided with any number of safety devices, shrouds, dispensing members, etc, that otherwise would interfere during accessing of the transfer device. Also, for very small or very large syringes, introduction horizontally can provide more stability for the user during use.

In aspects of the disclosed embodiments, an adapter comprising a pierceable elastomeric septum, is configured on the fluid delivery container for providing fluidic communication with the fluidic conduit system. In one aspect, the adapter aligns the pierceable septum perpendicular to the axis of the fluid delivery container. Upon actuation of the transfer system, the septum is pierced via a fluid delivery container access providing fluid communication of the fluid delivery container with the fluidic conduit system.

In other aspects of the disclosed embodiments, the fluid transfer and delivery device in combination with any of the preceding aspects above may be configured with an elastomeric check valve.

In other aspects of the disclosed embodiments, the fluid transfer and delivery device in combination with any of the preceding aspects above may be configured with a collapsible elastomeric sleeve placed over the fluid delivery container accessing member sealing the opening of the fluid delivery container accessing member, preventing access to the fluidic conduit system prior to activation. Alternatively, the delivery device can be provided with a collapsible elastomeric sleeve placed over the delivery device dispensing member, (e.g., a needleless connector or lumen spike) sealing the opening of the dispensing member, preventing access to the fluidic conduit system prior to activation. In this aspect, for example, the dispensing member can be a male luer, male luer valve, sleeved-covered cannula, needle/blunt cannula, and the delivery device accessing member can be a pierceable septum, female luer valve, or female luer.

In one aspect, a multi-container transfer and delivery device is configured to allow multiple containers to transfer and mix their respective materials, and for receiving of the mixed materials to a fluid delivery device. The transfer system comprises a plurality of flow conduits for fluid flow between the multiple containers and the fluid delivery device. A drug mixing kit comprising a multi-container housing with a plurality of flow conduits, a plurality of compartments for receiving containers, and a fluid delivery device is described.

The multi-container transfer and delivery device disclosed and described herein can be operated easily and safely by the user, so that drug preparation and administration may be achieved by the user in a reduced number of steps. It can be inexpensively produced and assembled. The system is suitable for dissolving a medicament as with a reconstitution process, and also for mixing fluids, media, for transferring a gas, etc.

In one aspect, a multi-container transfer and delivery device is provided wherein the device comprises a collapsible housing which may include a first, an intermediate, and a final portion, each portion comprising at least one media container having respective media container accessing means (e.g., spike, blunted cannula, luer fitting, or the like, with one or more lumens) for sealably accessing the media containers via an external force. The containers may be integral with the device and may be sealably accessed by, but is not limited to, spike or cannula penetration, displacement of a deformable member for example, a needle-free valve, displacement of a rigid or semi-rigid member such as a luer fitting, or any combination of these or their like. One or more of the media containers may already be sealably accessed upon its manufactured device assembly e.g. a syringe connected via a luer fitting, prior to the user providing the external access force. The term "collapsible", as it pertains to the housing, may refer to being slidably received by the housing, deformable, telescoping, or any combination thereof. The transfer and delivery device media containers may include standard drug vials for the first and intermediate media containers, and a syringe for the final media container.

A first media container accessing means may comprise at least one first fluid lumen and optionally one vent lumen open proximal to its distal end; said vent lumen may terminate in a filtering means, such as hydrophobic vent media. Vent lumen or vent may also include a check valve alone or in combination with a vent media allowing essentially sterile or otherwise clean air to enter into the system.

An intermediate media container accessing means may comprise at least one intermediate fluid lumen and a second intermediate fluid lumen, each open proximal to its distal end. The at least one intermediate fluid lumen may be in communication with at least one first fluid lumen. The final may include a fluid delivery container, accessible by a final portion fluid delivery container accessing means. A final fluid delivery container accessing means may include a final fluid lumen open proximal to its distal end and may be in fluid communication with the second intermediate fluid lumen. The fluid delivery container may be reversibly connectable to the housing and may be, but is not limited to, a syringe. The fluid delivery container may be accessed through an integrated, penetrable septum or may be sealably connected by way of a standard male/female Luer arrangement which may be of the luer lock or luer slip. The housing may employ a locking mechanism for reversibly securing the fluid delivery container.

The multi-container transfer and delivery device can comprise varying container access member lengths, or may include varied gaps between container septums and access members, or similar means in the pre-access state in order to allow for sequencing of the first, intermediate, and final accesses upon application of an external force.

The multi-container transfer and delivery device in combination with any of the preceding aspects above can comprise a syringe with a needle safety mechanism.

The multi-container transfer and delivery device in combination with any of the preceding aspects above can comprise a flange at its base to allow for stable use on a generally flat, horizontal surface In a fourth aspect of the enclosed embodiment, the multi-container transfer and delivery device in combination with any of the preceding aspects above may comprise one or more slip-resistant members, e.g. foam pads or rubber bumpers, at its base.

The multi-container transfer and delivery device in combination with any of the preceding aspects above can utilize coatings and or lubrication e.g. silicone oil to reduce the external force required to activate the device and/or to reduce penetration forces of the accessing members and containers.

The multi-container transfer and delivery device in combination with any of the preceding aspects above can provide at least one mixing element in series with any of the first, intermediate or final conduits. The mixing element may be but not is limited to a static mixer.

The multi-container transfer and delivery device in combination with any of the preceding aspects above can be configured with an opening or access door such that a media container may be inserted by the user after manufacturing assembly. The multi-container transfer and delivery device in combination with any of the preceding aspects above may be configured with an access such that a media container may be passed therethrough and may therefore function as said media container within. Said media container may be any pre-packaged media container that may be accessible by any means appropriate to access members, for example a standard medicament vial or diluent vial having a septum able to be accessed by a container access member that may be a spike.

Thus, referring now to FIG. 1, a perspective view of transfer and delivery device 100 comprising upper housing 101 configured to accept syringe 102, which is secured by a locking means 103 and lower housing 104, is shown. Flange 105 is positioned about the base of the lower housing. Likewise, a flange may also be positioned about the upper housing.

Figure 2:
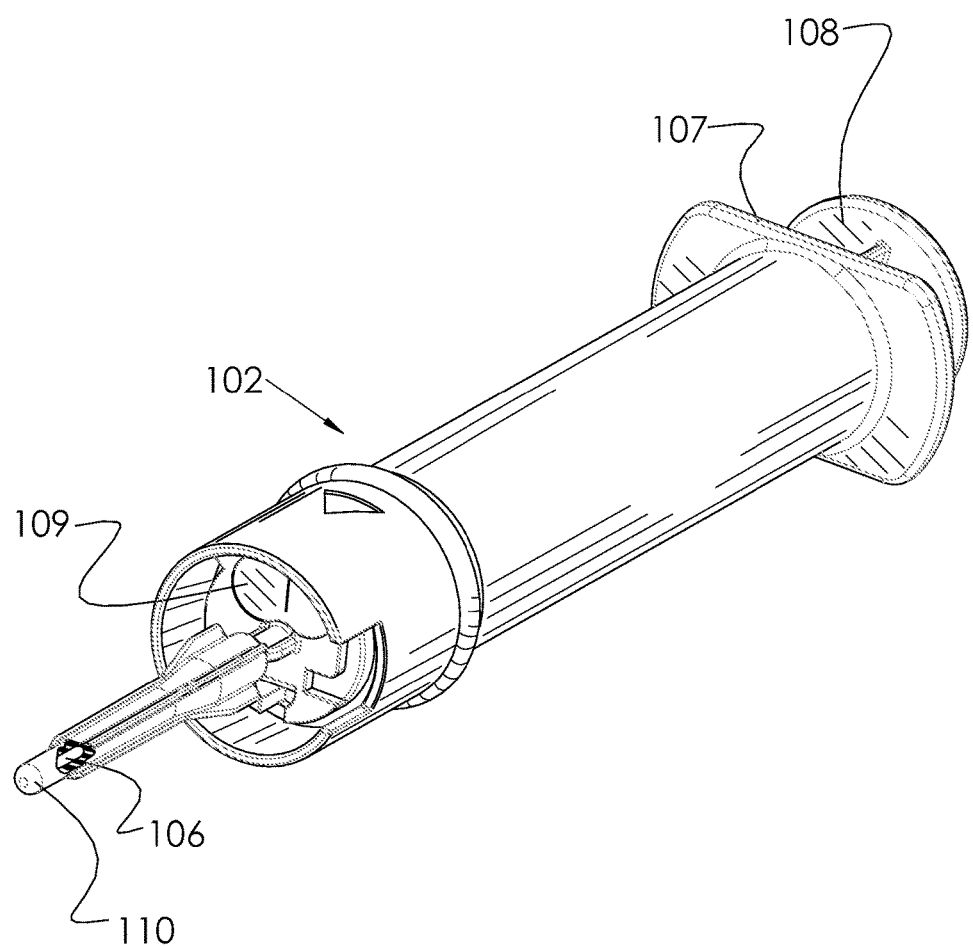
FIG. 2 is a perspective view of a detached delivery device as disclosed and described herein.
Figures 4A, 4B:
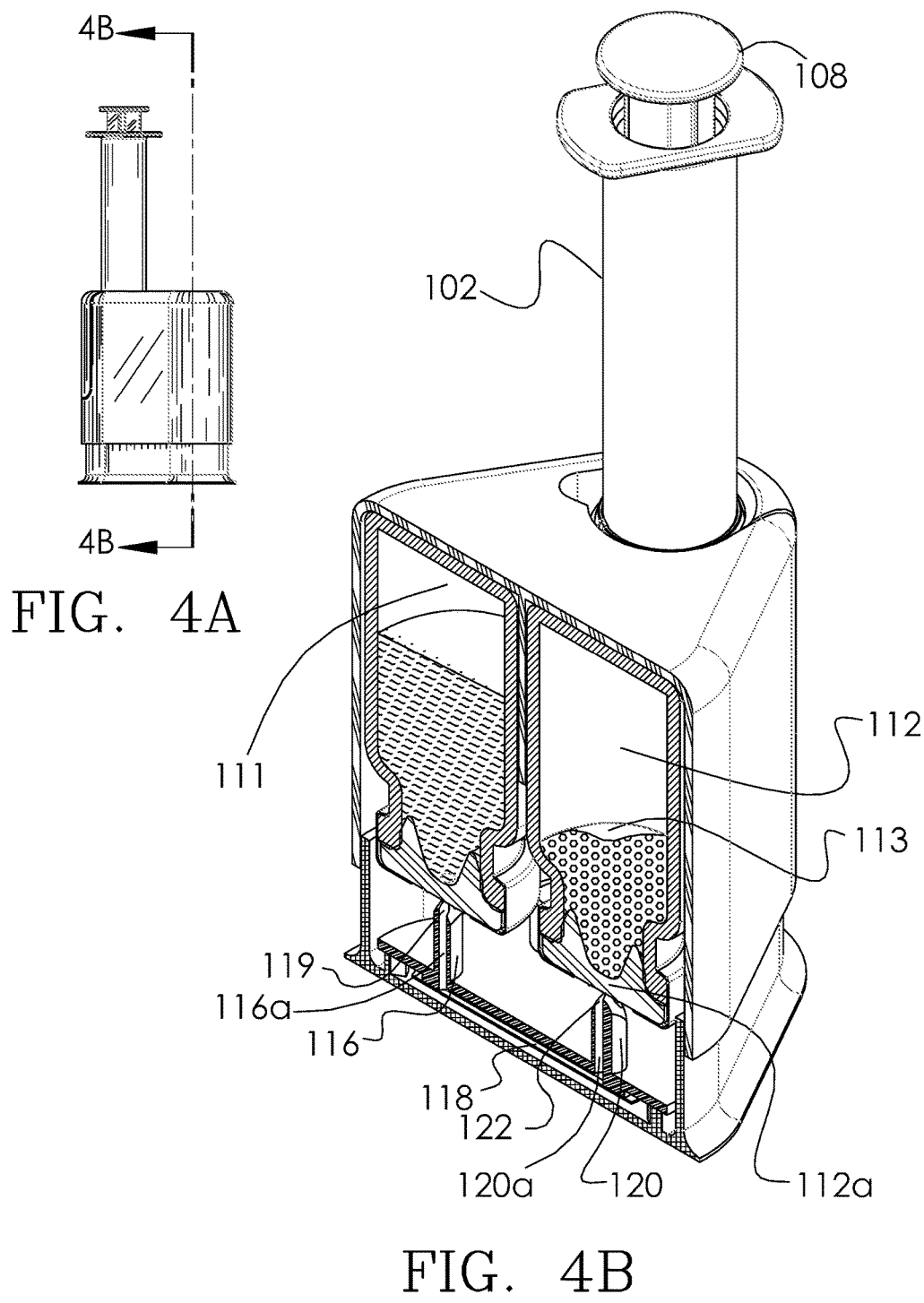
FIGS. 4A-4B are section plane and corresponding cross-sectional views of the transfer and delivery device of FIG. 1 in an initial state, as disclosed and described herein.
Figure 5A:
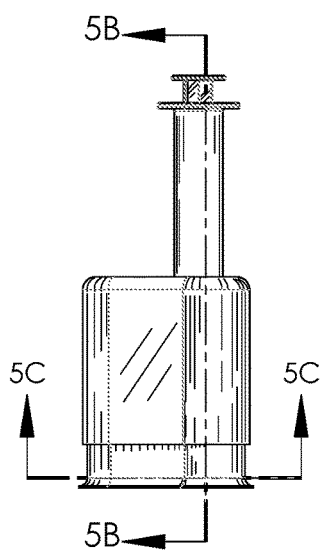
FIGS. 5A-5C are section plane and corresponding cross-sectional views of the transfer and delivery device of FIG. 1 in an initial state, as disclosed and described herein.
Figure 5B:
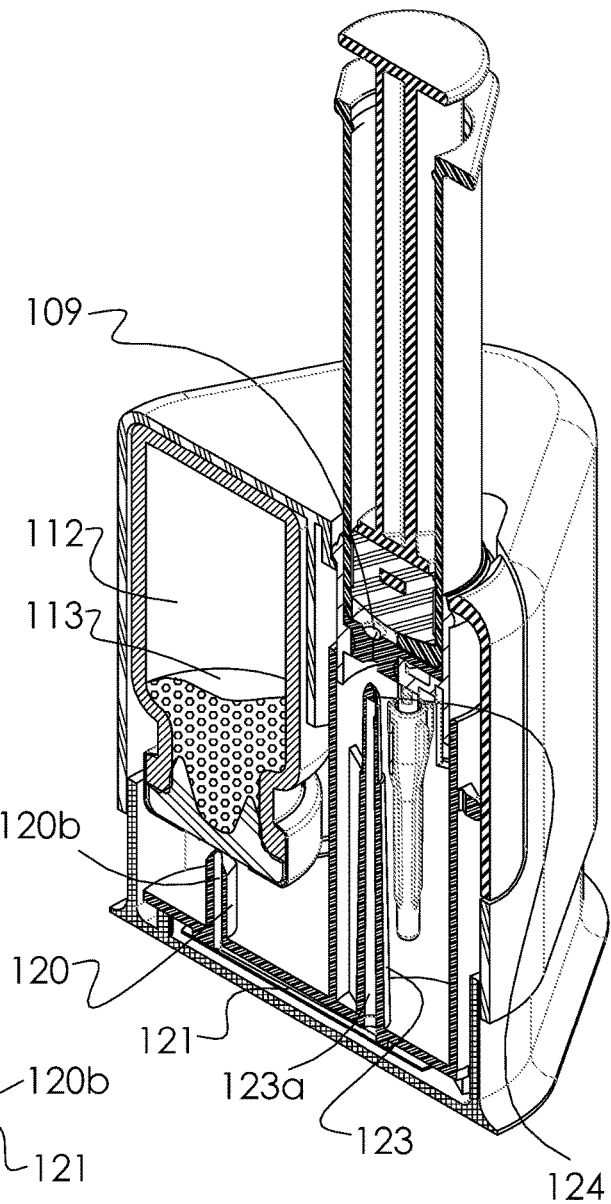
Figure 5C:
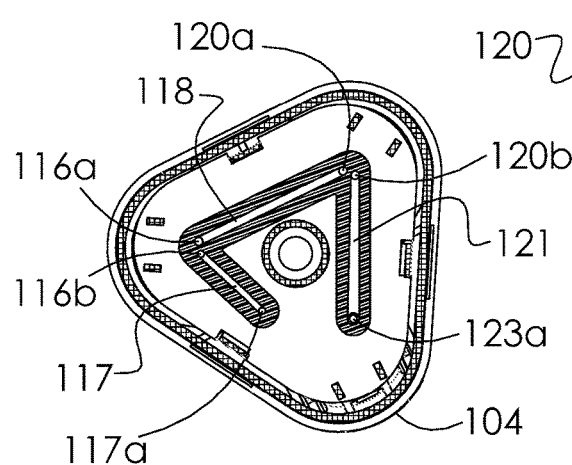

FIG. 2 is a perspective view of detached syringe 102 comprising a first end terminating in cannula/needle 106, second open end 107 for accepting a slidable plunger rod 108 for controlling interior volume and pressure, and penetrable septum 109 (by-pass element) positioned adjacent the needle, for allowing fluid communication with the interior volume of syringe. The first end needle is adapted to accept a removable, sealing needle cover 110 or, optionally, a needle safety mechanism not shown. Alignment features (not shown) can be used to allow syringe to assemble in a predetermined manner with upper housing 101.

FIGS. 3A-5C are section plane and corresponding cross-sectional views of the first embodiment in an initial state, detailing the flow conduits, spikes, and vent. Referring now to FIGS. 3A & 3B, first container 111 having penetrable septum 111a contains fluid 129. The syringe 102 of FIG. 2 is reversibly connected to the upper housing by locking feature 114 and loaded by cantilever spring 115, the locking feature integrated with or attached to the upper housing 101. First container accessing member 116 (also referred to as spike 116) terminates in a first point and comprises a first fluid lumen 116a (visible in FIG. 4B) and a vent lumen 116b, each open proximal to its distal end 119 (visible in FIG. 4B). Vent conduit 117 connects vent lumen 116b of spike 116 with vent 117a. Referring to FIGS. 4A & 4B, intermediate container 112, having a penetrable septum 112a, contains media 113, for example a reconstitutable or concentrated drug. Intermediate container accessing means 120 (also referred to as spike 120) terminates in a second point and comprises a first intermediate fluid lumen 120a and a second intermediate fluid lumen 120b (visible in FIG. 5B), each open proximal to distal end 122. First fluid conduit 118 connects first fluid lumen 116a with first intermediate fluid lumen 120a. Referring now to FIGS. 5A & 5B, final container accessing means 123 (also referred to as spike 123) terminates in a point or blunted cannula, and comprises fluid lumen 123a open proximal to its distal end 124. Second fluid conduit 121 connects second intermediate lumen 120b with final fluid lumen 123a.

Conduits 117, 118 and 121 are physically isolated from each other. The dual lumens of the spikes connect these isolated fluid conduits together to provide at least a portion of a fluidic conduit system. In one aspect, a fluidic conduit system is formed upon assembly of a base plate with the lower housing and provides fluid communication between at least two of the spikes or a spike and the vent of the device. Thus, vent lumen 116b of spike 116, vent conduit 117, and vent 117a are in fluidic communication. Fluid lumen 120a of spike 120, first fluid conduit 118, and fluid lumen 116a of spike 116 are in fluidic communication. Fluid lumen 123a of accessing means 123, second fluid conduit 121, and fluid lumen 120b of spike 120 are in fluidic communication.

FIGS. 6A-6D are section plane and corresponding cross-sectional views of the first embodiment device in its activated state. Access members have sealably pierced their respective media containers. Fluid communication is made between the vent conduit 117, first container 111, first fluid conduit 118, intermediate container 112, second fluid conduit 121 and interior volume 125 of syringe 102. First container contains fluid 129, as shown, just prior to its fluid being pulled into the intermediate container.

Figure 6A:
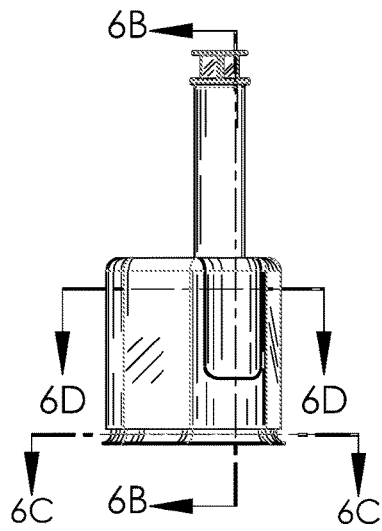
FIGS. 6A-6D are section plane and corresponding cross-sectional views of the transfer and delivery device of FIG. 1 in an activated state, as disclosed and described herein.
Figure 6C:
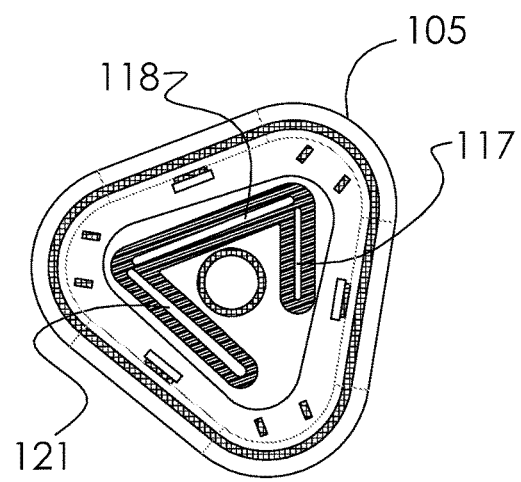
Figure 6B:
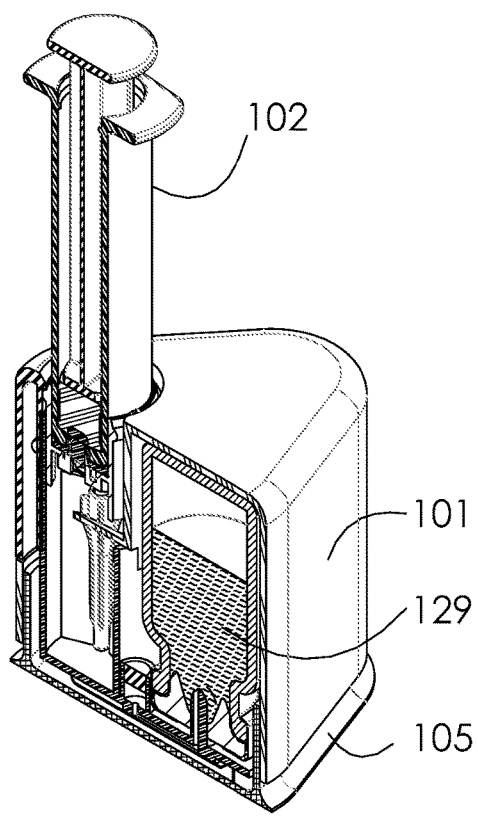

FIG. 6C illustrates a sectioned top view of lower housing element flange 105, which when overlaid with base plate (not shown, see, e.g., FIG. 11B, callout 333), creates the isolated fluid conduits 117, 118, and 121 from formed channels.

Figure 6D:
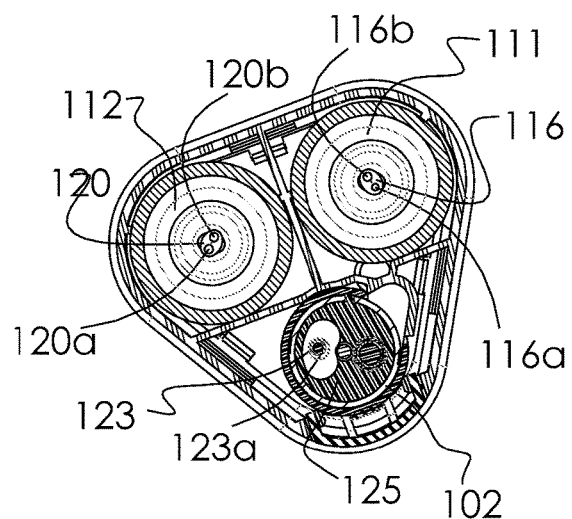

FIG. 6D shows the sectional view of the upper housing revealing lumens 116a, 116b of spike 116, lumens 120a, 120b of spike 120, and lumen 123a of spike 123.

Figure 7A:
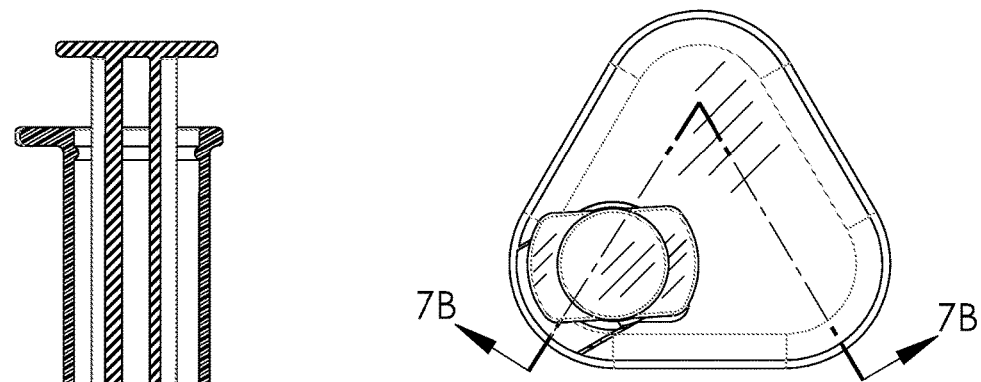
FIGS. 7A-7B are section plane and corresponding cross-sectional views of the transfer and delivery device of FIG. 1 in an immediate activated state, as disclosed and described herein.
Figure 7B:
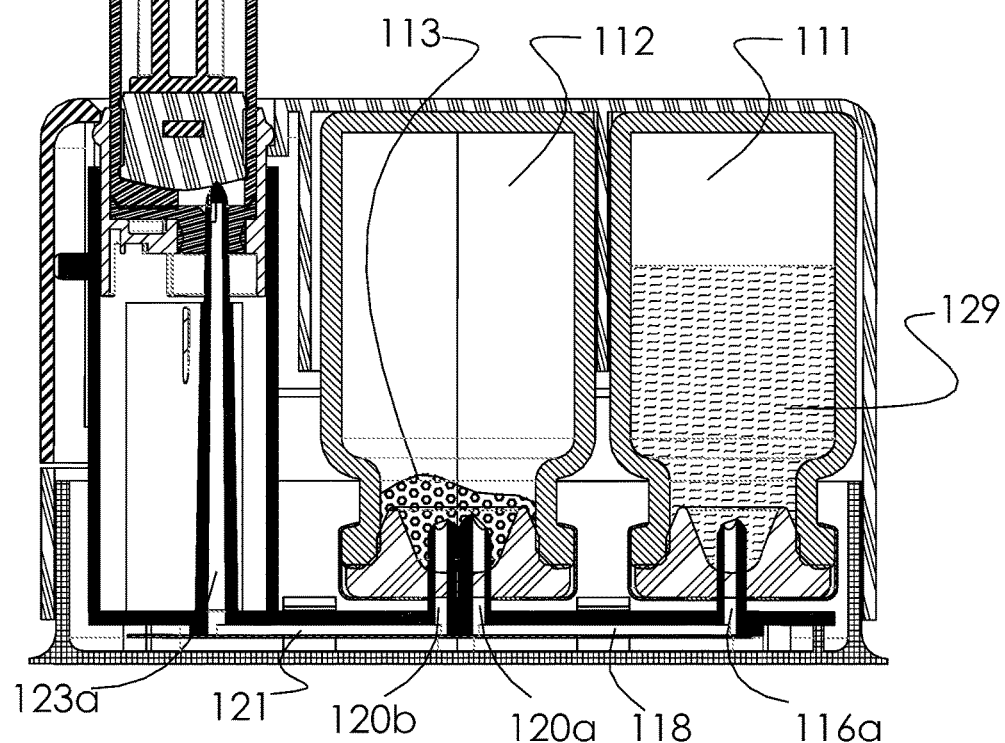

FIGS. 7A-7B are section plane and corresponding cross-sectional views of the first embodiment device in its activated state, in a theoretical instance just before any fluid transfer has taken place. Container accessing members 116, 120, and 123 (FIG. 6D) have sealably pierced their respective media containers 111, 112, and 102, providing fluid communication between vent, vent conduit (FIG. 6D), first container 111 containing fluid 129, first fluid conduit 118, intermediate container 112 containing drug media 113 under vacuum, second fluid conduit 121, and syringe 102.

Figure 8A:
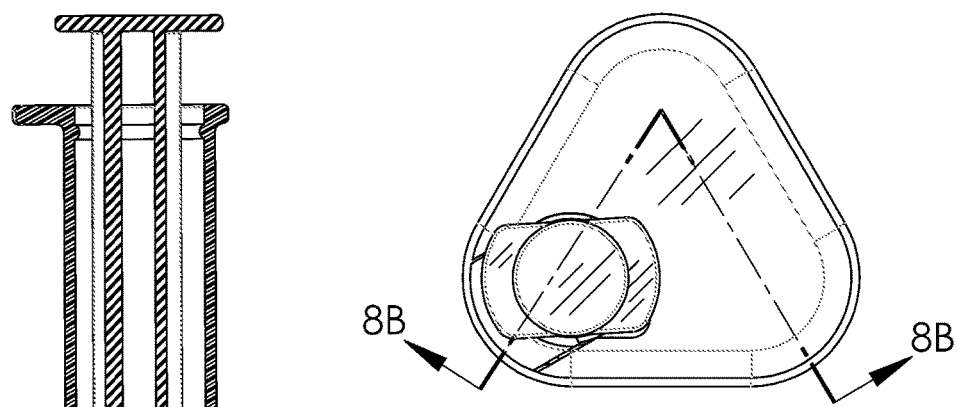
FIGS. 8A-8B are section plane and corresponding cross-sectional views of the transfer and delivery device of FIG. 1 in its activated state a moment after the state as depicted in FIG. 7B.
Figure 8B:
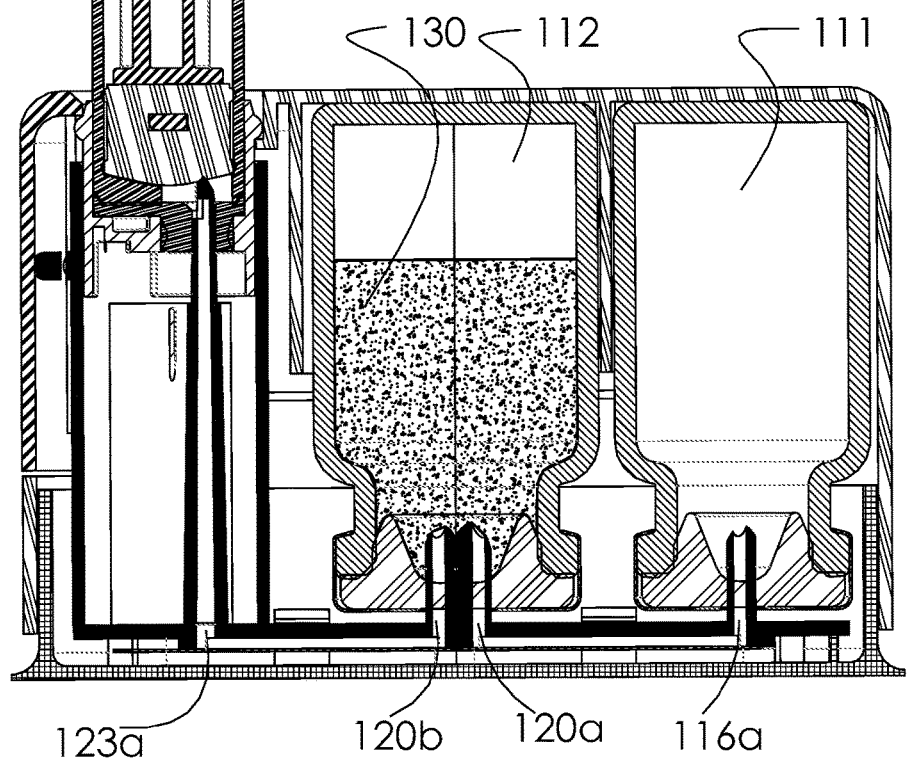

FIGS. 8A-8B are section plane and corresponding cross-sectional views of the first embodiment device in its activated state a moment after the state depicted in FIG. 7B, where the pre-existing vacuum of second container 112 has drawn in the fluid from first container 111 and has allowed the fluid to mix with the drug media in second container 112, providing drug mixture 130, which can be a solution, suspension, dispersion oil-in-water or water-in-oil, gel, and the like. As shown, each of the elongate container accessing members (i.e., 116, 120) and the delivery device accessing member 123 project in the same direction relative to the base of the lower housing.

Figures 9A, 9B:
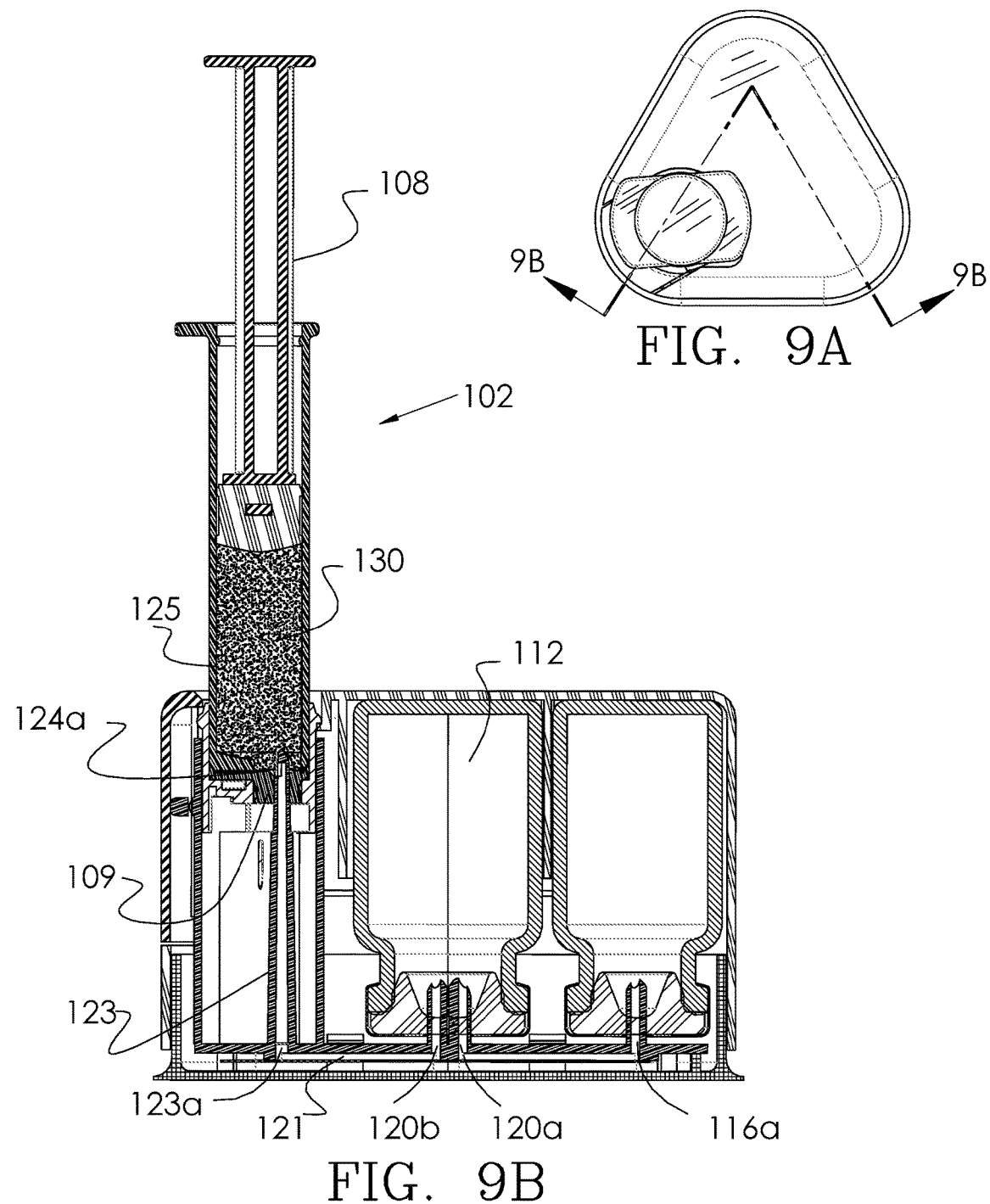
FIGS. 9A-9B are section plane and corresponding cross-sectional views of the transfer and delivery device of FIG. 1 in an activated state.

FIGS. 9A-9B are section plane and corresponding cross-sectional views of the first embodiment device in its activated state, where drug mixture 130 has been drawn from the second container 112 into syringe 102 interior volume 125 by drawing back syringe plunger rod 108. The drug mixture has passed through fluid lumen 123a of accessing member 123 which is sealably penetrating by-pass element (septum 109) and into the syringe interior volume 125 via conduit opening 124a. Displaced volume of fluid container 111 is accommodated via vent 117a (see FIG. 3B).

Figure 10A:
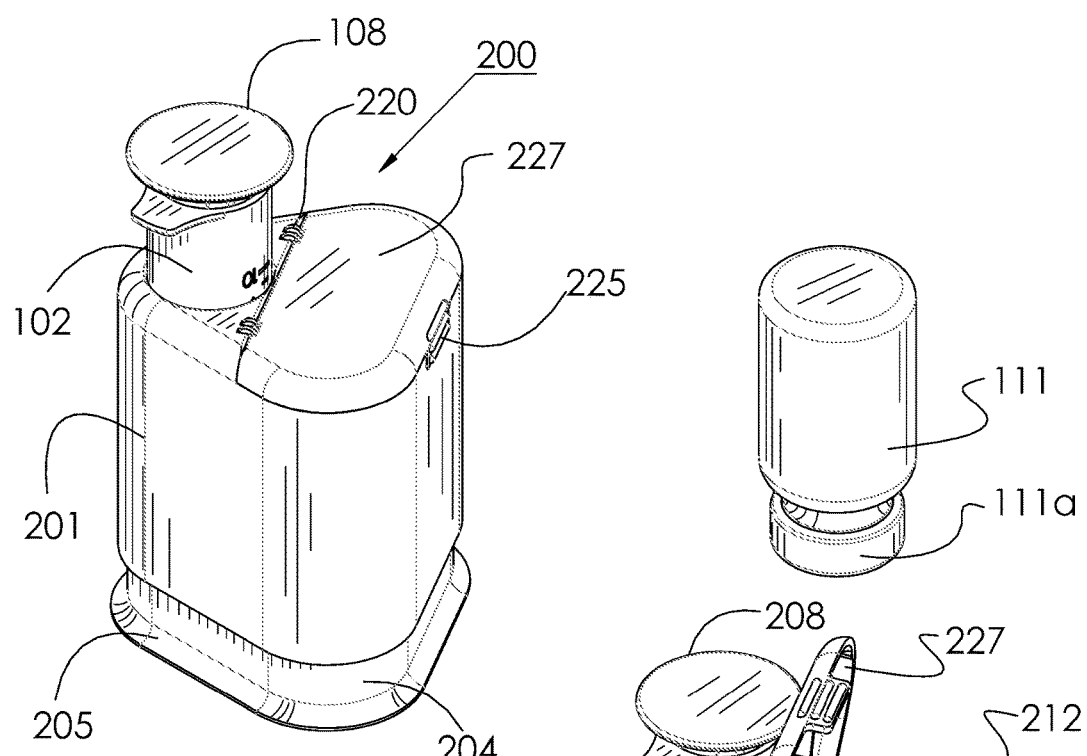
FIGS. 10A-10B are perspective views of an alternative embodiment of a transfer and delivery device, as disclosed and described herein.
Figure 10B:
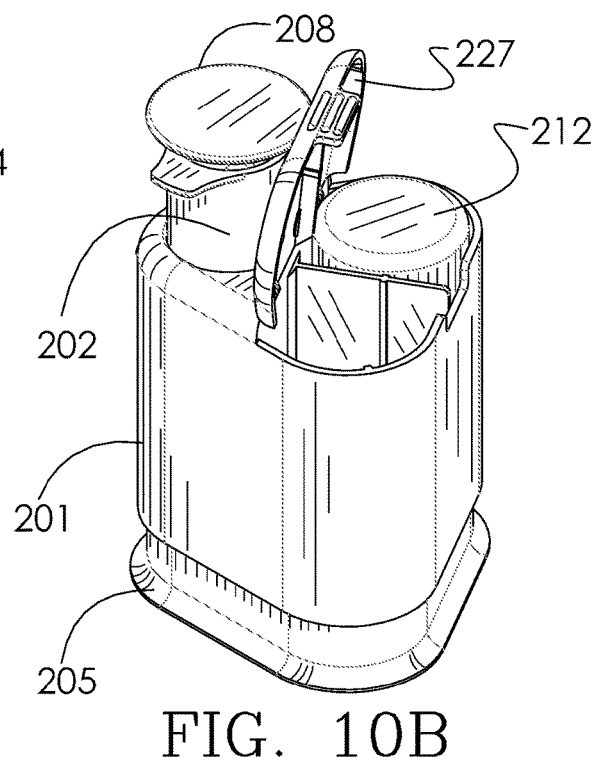

FIGS. 10A-10B are perspective views of a second embodiment fluid transfer and delivery device 200 having base flange 205 supporting lower housing 204, which slideably receives upper housing 201, in which the first media container 111 and second media container 112 can be added, removed or exchanged by means of an access 227 with hinge means 220 and latch means 225. Syringe 102 with plunger rod 108 is provided as above.

FIGS. 11A-11B are a perspective view and exploded view of a third embodiment of device 300 having upper housing 301 slideably received by lower housing 304, with alignment means 301a and 304a, respectively. Syringe release catch 303b is adapted to top 301b of upper housing 301 to serve as reversible locking means for the syringe 302b. Optional gripping features 328a and 328b can be added to the top and sides of the upper housing. Syringe 302b has a passive needle safety feature 350. FIG. 11B depicts the exploded view with the relationship between the syringe, containers and fluid conduit system of device 300. Additional incidental details of this design depicted in FIGS. 11A & 11B, including detents 331a, 331b in top 301b of upper housing 301 that interacts with the syringe release catch to create an "open" and "closed" position, respectively; locking feature 332 on the lower housing 304 that interacts with a corresponding catch feature on the upper housing to hold the components together in the as-assembled and accessed positions. Also shown are the three spikes 316b, 320b, 323b that pierce the septums 111a, 112a of media containers 111, 112, respectively and syringe septum of syringe 302b respectively; end of the vent conduit 317b, and the flat sheet or film component 333, that when overlaid with the lower housing 304 with integrated channels, forms the flow conduits 317, 318, and 321 (not shown) connecting the corresponding lumens in spikes 316b, 320b, 323b and vent conduit 317b.

FIGS. 12A-12C are an orthogonal, top and section view respectively of fourth embodiment device 400 having upper housing 401 slidably engaging lower housing 404, and fluid conduit 421 with syringe securing member 434 with lumen 423a in the lower housing 404 for connecting syringe 402 with plunger 408. Device 400 lacks a piercing syringe accessing member and is adapted with a syringe accessing member suitable for securing a conventional syringe to the lower housing, specifically, a syringe securing member. Syringe securing member may include, for example, a luer-lok adapters, luer fittings, and other threaded or tolerance fittings. Guide features/locking means 444, 435a, and 435b, together with container locking features 411a, 412a secures upper and lower housings and containers in the as-assembled and accessed positions.

FIGS. 13A-13C are perspective view and exploded view of the fourth embodiment device 400. In FIG. 13A the upper housing includes access 427 to enable loading of the media containers 111, 112 and gripping features 428a have been added to the top of the upper housing. The access may be comprised of two or more separate components, hinged at one or more locations, or may be included in the upper housing with one or more living hinge features. In the exploded view FIG. 13B the relationship between these components can be seen. Guide feature 444 in the lower housing 404 supports the upper housing 401b, locking features 435a, 435b in the lower housing interacts with corresponding catch features 436 on the upper housing to hold the components together in the as-assembled and accessed positions. The upper housing also includes undercut securing features 437a, 437b for receiving container septum 111a, 112a portions. Also shown are two spikes 416a, 420b that pierce media containers 111, 112 pierceable septums. Syringe 402 is shown connected to a luer connection 438 adjacent to vent 417b. As shown, each of the container accessing members (i.e., 416a, 420b) and the delivery device accessing member (i.e., luer connection 438) project in the same direction relative to the base of the lower housing. Base plate 433 comprised of aflat sheet or film component that when overlaid with the lower housing 404 closes the molded channels 417c, 418c, and 421c (referring to perspective view of lower housing 404, FIG. 13C) to form the fluid conduits 417, 418, and 421 (not shown) for fluid communication with lumens of spikes 416a, 420b and luer connection 438 and vent 417b. Fluid conduits 417, 418 and 421 are physically isolated from each other. The dual lumens of the spikes connect these isolated fluid conduits together, to provide at least a portion of a fluidic conduit system. In one aspect, a fluidic conduit system is formed upon assembly of flat sheet or film component base plate 433 with the lower housing 404 and provides fluid communication between at least two of spikes and/or compartments of the device.

FIGS. 14A-14B are perspective views of fluid transfer and delivery device 400 in which the first media container 111 and second media container 112 can be added, removed or exchanged by means of an access 427 with hinge means for providing opening for receiving the container septums 111a, 112a of containers 111, 112 respectively.

In use, to transfer fluid between the first and intermediate containers in device 400, mix or dissolve the drug, and transfer the mixture to the syringe for administration or dispensing, a external force, typically by the hand of a user, is employed to telescopically collapse the upper housing into the lower housing of the device and subsequently allow the media container accessing spikes to pierce their respective media containers. Vacuum preconditioned in the second container as is often found in lyophilized drug vials, for instance creates a pressure differential when sealably accessed thereby causing the fluid of the first container to fluidically navigate the first fluid conduit and be deposited into the intermediate media container. At this time, filtered air is likewise drawn into the first container for pressure equalization via the vent conduit. The contents of the intermediate container may then be agitated in a manner appropriate to the mixture. Drawing back on the syringe plunger rod creates a pressure differential between the intermediate container and the interior of the syringe causing the mixed drug to fluidically navigate the second fluid conduit and be deposited into the interior volume of the syringe. At this time, filtered air is likewise drawn into the system by way of the vent conduit and subsequent conduits for pressure equalization.

Figure 15A:
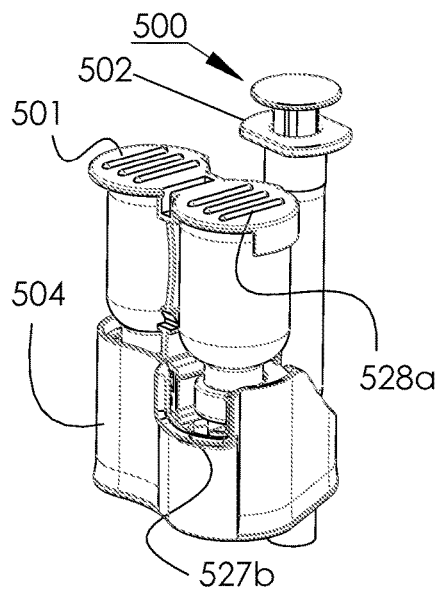
FIGS. 15A-15B are a perspective view and exploded view of an alternative embodiment of the transfer and delivery device as disclosed and described herein.
Figure 15B:
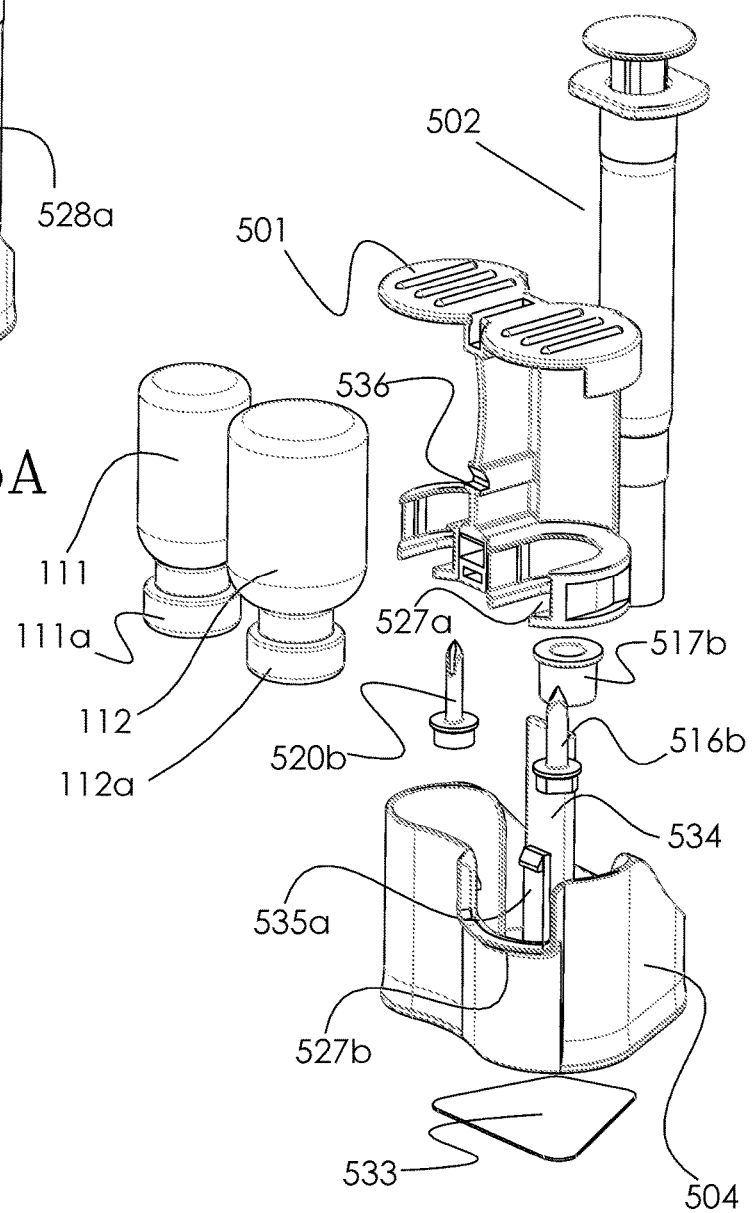

FIGS. 15A-15B are a perspective view and exploded view, respectively, of a fifth embodiment device 500. In FIG. 15A the upper housing 501 is received by lower housing 504, which includes container access cutout 527b to enable loading of only one container (e.g., container 112) after manufacturing assembly. Gripping features 528a have been added to the top of the upper housing. In the exploded view FIG. 15B the relationship between these components can be seen. Guide feature 534 in the lower housing 504 supports the upper housing. Locking features 535a in the lower housing interact with corresponding catch features 536 on the upper housing to hold the components & housing sections together in the as-assembled and accessed positions. Also shown are two spikes 516b, 520b that pierce media containers 111, 112 pierceable septum's respectively. Spikes 516b, 520b are received by lower housing 504 and maintained by methods including but not limited to ultrasound welding, adhesives, press-fitting, solvent bonding, and the like. Syringe 502 is received by connection not shown in lower housing 504. Flat sheet or film component 533 when overlaid with the lower housing 504 closes the molded channels to create the fluid conduits 517, 518, and 521 not shown creating the corresponding fluid conduits connecting spikes 516b, 520b, vent 517b and connection for syringe not shown. In use, the user must first load the intermediate media container (which may contain a drug) into the device by inserting it into the container access 527a, 527b. Then to transfer fluid between the first and intermediate containers in device 500, mix or dissolve the drug, and transfer the mixture to the syringe for administration or dispensing, an external force, typically by the hand of a user, is employed to urge the upper housing (e.g., telescopically collapse) into the lower housing of the device and subsequently allow the media container accessing spikes to pierce their respective media containers. Vacuum preconditioned in the second container as is often found in lyophilized drug vials, for instance creates a pressure differential when sealably accessed thereby causing the fluid of the first container to fluidically navigate the first fluid conduit and be deposited into the intermediate media container. At this time, filtered air is likewise drawn into the first container for pressure equalization via the vent conduit. The contents of the intermediate container may then be agitated in a manner appropriate to the mixture. Drawing back on the syringe plunger rod creates a pressure differential between the intermediate container and the interior of the syringe causing the mixed drug to fluidically navigate the second fluid conduit and be deposited into the interior volume of the syringe. At this time, filtered air is likewise drawn into the system by way of the vent conduit and subsequent conduits for pressure equalization.

Packaging

In another aspect, the above device embodiments are packaged in a way such that a container comprising a sterilizing-sensitive media can be packaged separately with a pre-sterilized device. In this way, the sterilizing-sensitive media to be dissolved, reconstituted or otherwise combined with the contents of a second container, for example a diluent or solvent, can be packaged together with the device. In another aspect, the device and at least one container can be assembled in a kit and packaged under aseptic conditions, for example, to provide a combination of containers (e.g., media and diluent).

Figure 16A:
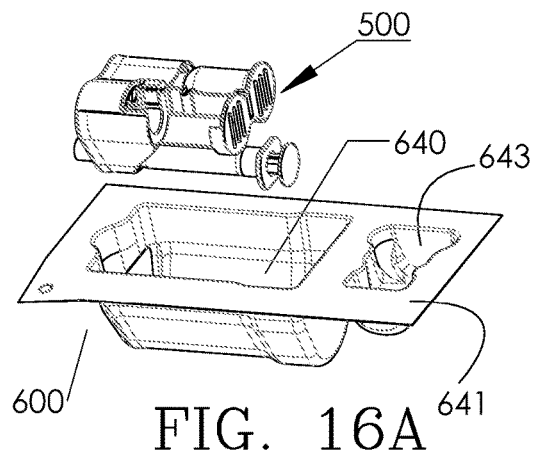
FIGS. 16A-16E are perspective views of a packaging system for the transfer and delivery device as disclosed and described herein.
Figure 16B:
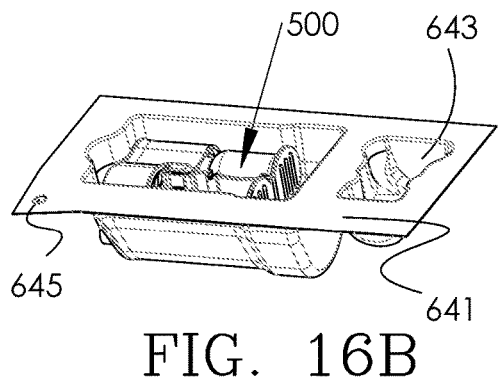
Figure 16C:
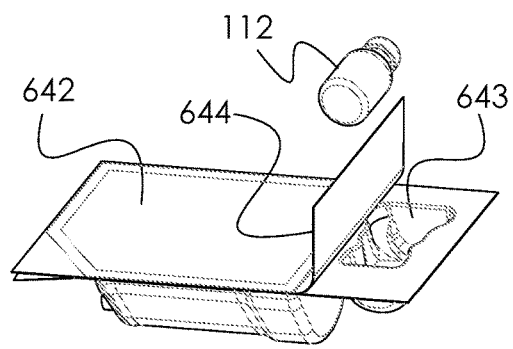
Figure 16D:
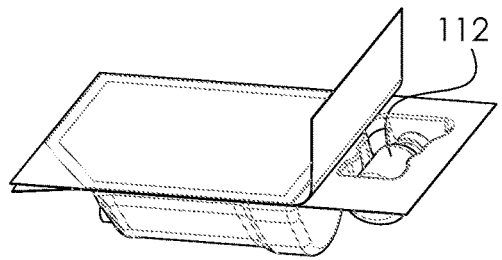
Figure 16E:
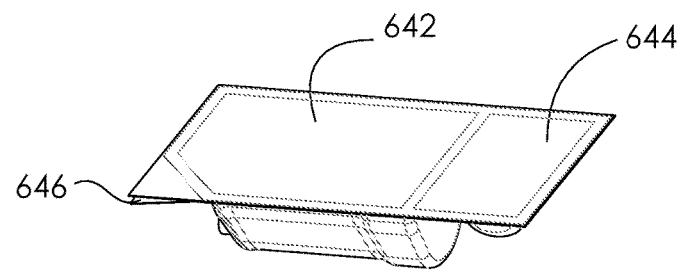

Thus, referring to FIG. 16A, partitioned packaging element 600 comprising first receptacle 640 adapted for receiving the device, e.g., 500 with optional liquid containing first container, is shown. FIG. 16B depicts device 500 received by package with raised feature 645 on face 641. FIG. 16C depicts lid 642 sealably configured to face 641 with un-sealed portion 644 aligned with second receptacle 643 adapted for receiving sterilizing-sensitive media of second container 112. Lid can be of continuous construction or can be provided in separate components adapted for the corresponding receptacles. Prior to receipt of sterilizing-sensitive media of container 112, the packaging element 600 with device and optional liquid container can be sterilized, for example, by high energy radiation, hydrogen peroxide, or ethylene oxide. Subsequent to the sterilization of packaging element 600 with device 500 and optional liquid container, the sterilizing-sensitive media of second container 112 can be received by second receptacle 643, optionally under aseptic conditions. Raised feature 645 allows for assistance with opening. FIGS. 17A-17E depicts packaging element 600 with first lid 642a configured to seal only first receptacle 640. Subsequent to the sterilization of packaging element 600 with device 500 and optional liquid container, the sterilizing-sensitive media of second container 112 can be received by second receptacle 643, and sealed with second lid 647. Lids 642 and/or 647 can be of any suitable material, for example peelable film or Tyvek®, for ease of release from face of packaging member or can be of a paper construct for pushing the device and/or container through.

FIGS. 18A-18D depicts the releasing of the sheet from the tray via separated section 646 of packaging element 600 (FIG. 16A) caused by raised feature, and introduction of the sterilizing-sensitive media of container 112 into device 500 via container access cutout 527.

Figure 18A:
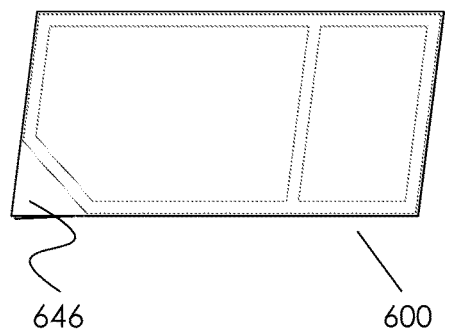
FIGS. 18A-18D are perspective views of a packaging system for the transfer and delivery device as disclosed and described herein.
Figure 18B:
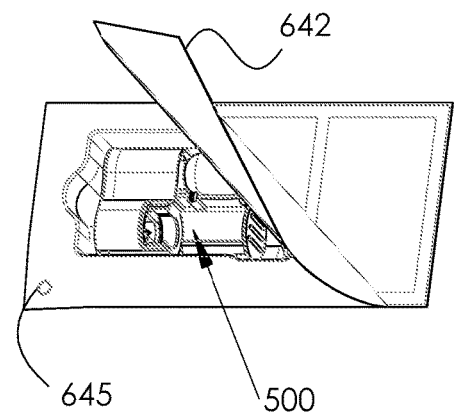
Figure 18C:
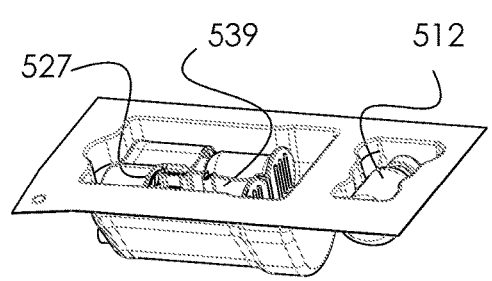
Figure 18D:
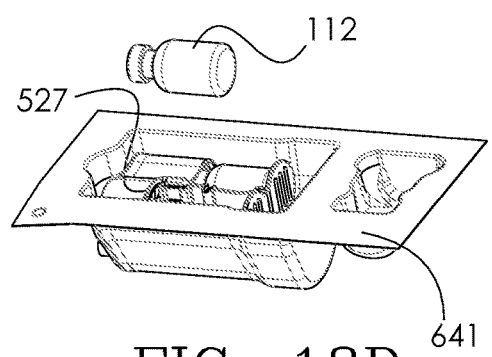
Figure 18E:
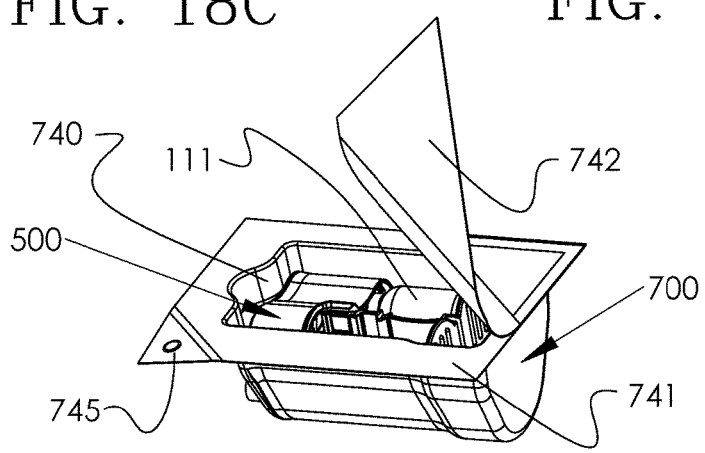
FIG. 18E is a perspective view of a packaging system for the transfer and delivery device and first container without second container.

FIG. 18E depicts an embodiment of kit 700 comprising any of the previously described transfer devices (e.g., 500 as shown) and first container 111, which can contain a suitable diluent, solvent, or other transferable substance. Package 741 provides a suitable receptacle for the transfer device and first container and comprises releasing lid 742 and releasing aid 745. Thus, the kit provides for packaging the transfer device with only the diluent for a substance that is to be provided separately at some later point in time. Kit 700 also provides for sterilization methods otherwise unacceptable to certain medicaments, for example, biologics. Upon use, the end-user would release the transfer device and associated (or pre-assembled, un-accessed) first container assembly from the receptacle and introduce the medicament (e.g., for dilution or for reconstitution) into the upper housing 501, which includes container access cutout 527 to enable loading of only one container (e.g., 112, which can comprise medicament (not shown)). Activation of the device as described above for device 500 provides for the transfer and mixing of the components of containers, e.g., 111 and 112.

Figures 19A, 19B:
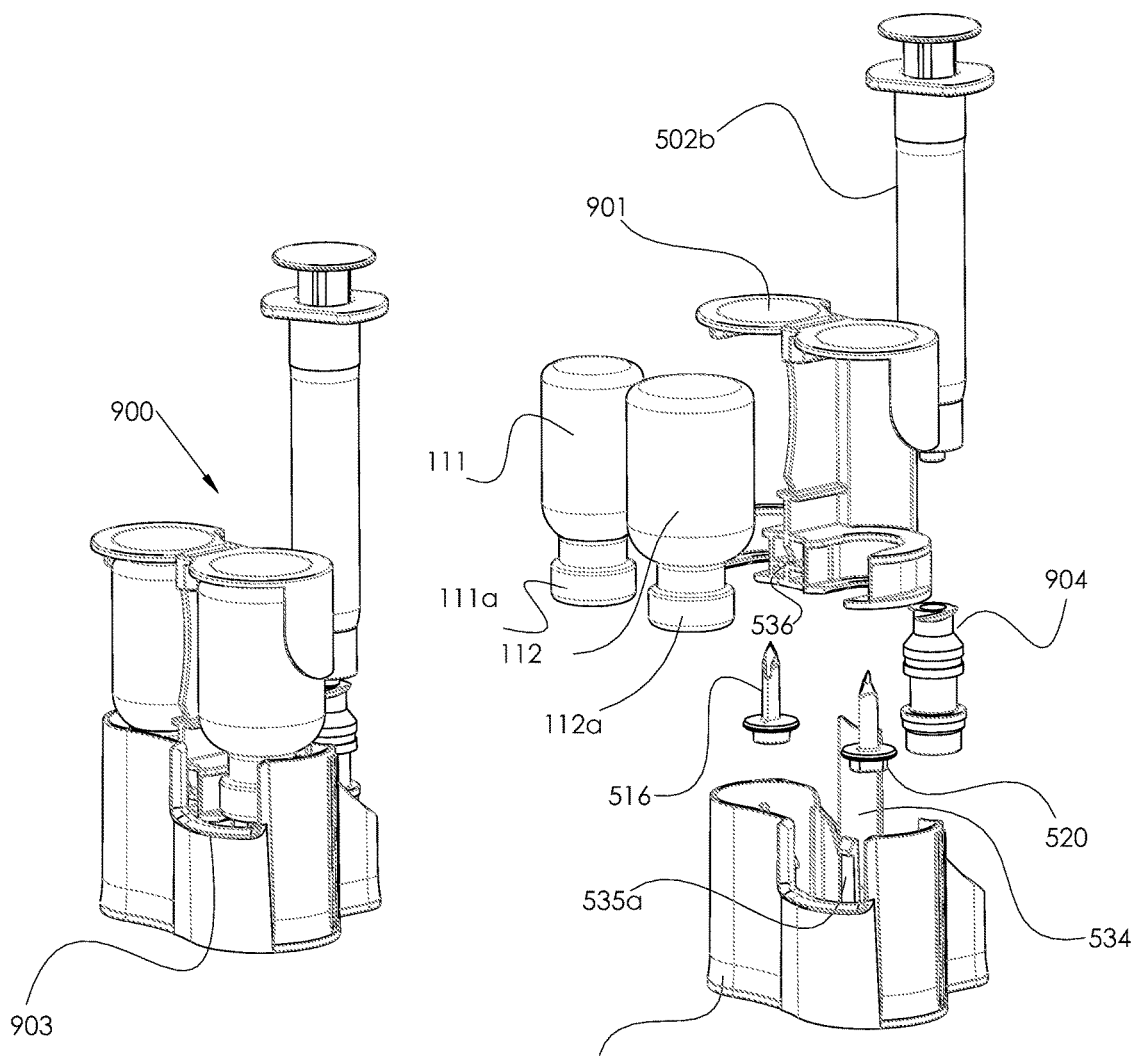
FIGS. 19A-19B are a perspective view and exploded view of an alternative embodiment of the fluid transfer and delivery device as disclosed and described herein.

FIG. 19A-19B are perspective view and exploded view, respectively, of an alternate embodiment transfer device 900, that provides, in one aspect, for activation of device 900 with or without an attached, conventional delivery device, while maintaining a closed fluidic system. In another aspect, device 900 allows for metering and/or repeated access of the contents of containers 111, 112 after activation of device 900. Thus, in one aspect the fluidic conduit system of device 900 comprises a valved access connector 904 that provides for control of the fluidic communication between delivery device 502b and the fluidic conduit system of device 900. In FIG. 19B the upper housing 901 is received by lower housing 902, which includes access 903 to enable loading of only one container 112 after assembly. Guide feature 534 in the lower housing 902 supports the upper housing. Locking features 535a in the lower housing interacting with corresponding catch features 536 on the upper housing to hold the components & housing sections together in the as-assembled and accessed positions. Also shown are two container accessing members 516b, 520b (e.g., spikes) that pierce media containers 111, 112 pierceable septum's 111a, 112a, respectively, assembled as described above. Fluid delivery container 502b is reversible received by a valved access connector 904 (e.g., valved female luer) coupled to connection 905 (as shown in FIG. 20B) in lower housing 902. Cavity (not shown) configured to receive check valve 807 is provided on the underside of the base of lower housing 902. Optional filter 811 is configured for placement between check valve 807 and fluid conduit 517. Filter 811 can also be inserted prior to check valve in cavity. Base plate 533 of flat sheet or film component closes the molded channels when overlaid with the lower housing 902 to create the fluid conduit system comprising fluid conduits, that forms fluid conduits 517, 518, and 521, accessible by accessing members 516b, 520b and lumen(s) of accessing member 808 for delivery device 502b and vent conduit (not shown). Valved connector 904 and optional check valve 807 provide for a closed system that can be accessed using, for example, a conventional syringe with, for example, a valved male luer, for mixing and/or transfer of a mixed media. Examples of such valved connectors include, needless CLAVE® connector (ICU Medical), SmartSite® (CareFusion), and Ultrasite® (B Braun).

To use device 900, containers 111 and 112 are assembled in upper housing 901 and arranged in a vertical, slidably configuration with lower housing 902 to slidably urge the upper housing towards the lower housing of the device and subsequently allow media container accessing spikes to pierce their respective media containers. Vacuum in the second container, as is often found in lyophilized drug vials, creates a pressure differential when sealably accessed thereby causing the fluid of the first container to fluidically navigate the first fluid conduit and be deposited into the intermediate media container. At this time, filtered air is likewise drawn into the first container through the check valve for pressure equalization via the vent conduit. The contents of the intermediate container may then be agitated in a manner appropriate to the mixture. Fluid delivery container 502b (e.g., syringe) is coupled to valved access connecter 904, (or may be previously coupled to lower housing) to allow fluidic communication with the fluidic system of device 900. Drawing back on the syringe plunger rod creates a pressure differential between the intermediate container and the interior of the syringe causing the mixed drug to fluidically navigate the second intermediate fluid conduit and be deposited into the interior volume of the syringe. At this time, filtered air is likewise drawn into the system by way of the vent conduit and subsequent conduits for pressure equalization. User applies a negative force in the fluid deliver container 502b, e.g., by drawing the plunger back, so that fluid is transferred between the first and intermediate containers in device 900, to mix or dissolve the drug followed by transferring of the mixture to delivery device 502b. Fluid delivery container 502b can then be decoupled from valved access connector 904 for administration or dispensing, whereby valved access connector 904 reversibly sealing fluidic system of device 900.

In another aspect, the transfer system including device 900 can be used with media containers that are not under reduced pressure as follows. First containers 111 and 112 are assembled in upper housing 901 and arranged in a vertical, slidably configuration with lower housing 902 to slidably urge the upper housing towards the lower housing of the device and subsequently allow media container accessing spikes to pierce their respective media containers. Plunger of delivery device 502b is drawn back to provide a desired displacement volume and then connected to valved access connector 904. Displacement volume from delivery device 502b is introduced into the fluidic system of device 900 cause mixing of fluid and media of containers 111 and 112. Withdrawal of mixture is achieved by creating reduced pressure using plunger of delivery device 502b.

Figure 20A:
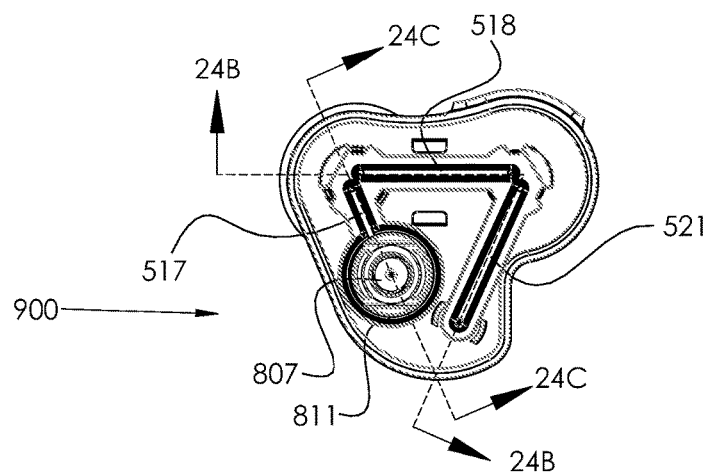
FIGS. 20A, 20B, and 20C are section plane, and corresponding cross-sectional views, respectively, of the fluid transfer and delivery device of FIG. 23A in an activated state.
Figure 20B:
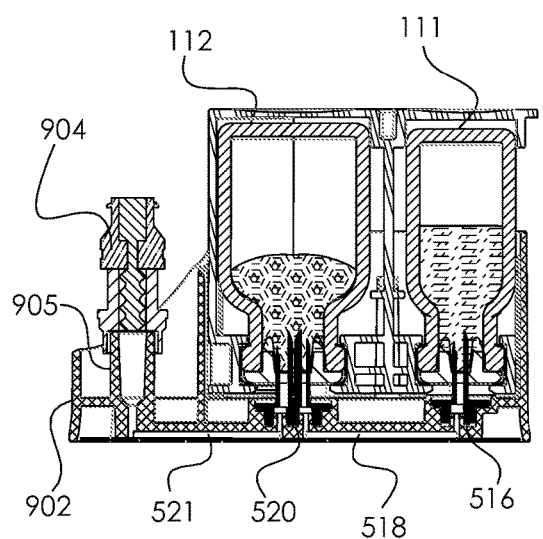
Figure 20C:
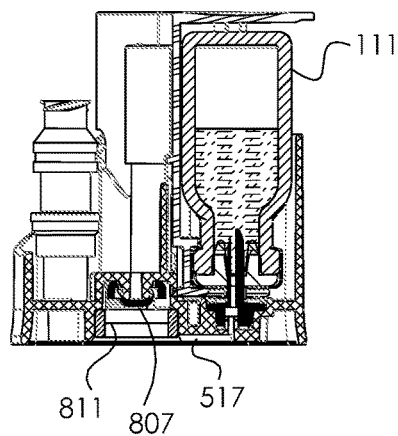

FIG. 20A-20C are section plane and corresponding cross-sectional views of device 900 in its activated state, in a theoretical instance just before any fluid transfer has taken place. Access means 516 and 520 have sealably pierced their respective media containers 111 and 112 providing fluid communication between fluid conduit 518, first container 111 containing fluid 129, intermediate container 112 containing drug media 113 under vacuum, second intermediate fluid conduit 521 and a delivery device (not shown). When media containers 111 and 112 are accessed via 516 and 520, respectively, check valve 807 opens allowing air into the system. Filter 811, located between check valve 807 and fluid conduit 517, prevents materials greater than a predetermined pore size enter the system from the atmosphere and fluid from exiting the system. In order to maintain a closed system, valved connector 904 is located between a fluid deliver container (not shown) and fluid conduit 521. Suitable valved luers include those disclosed in co-assigned U.S. Published Application 2006/0192164.

Transfer Device with By-Pass Syringe Adapter

Figures 21A, 21B:
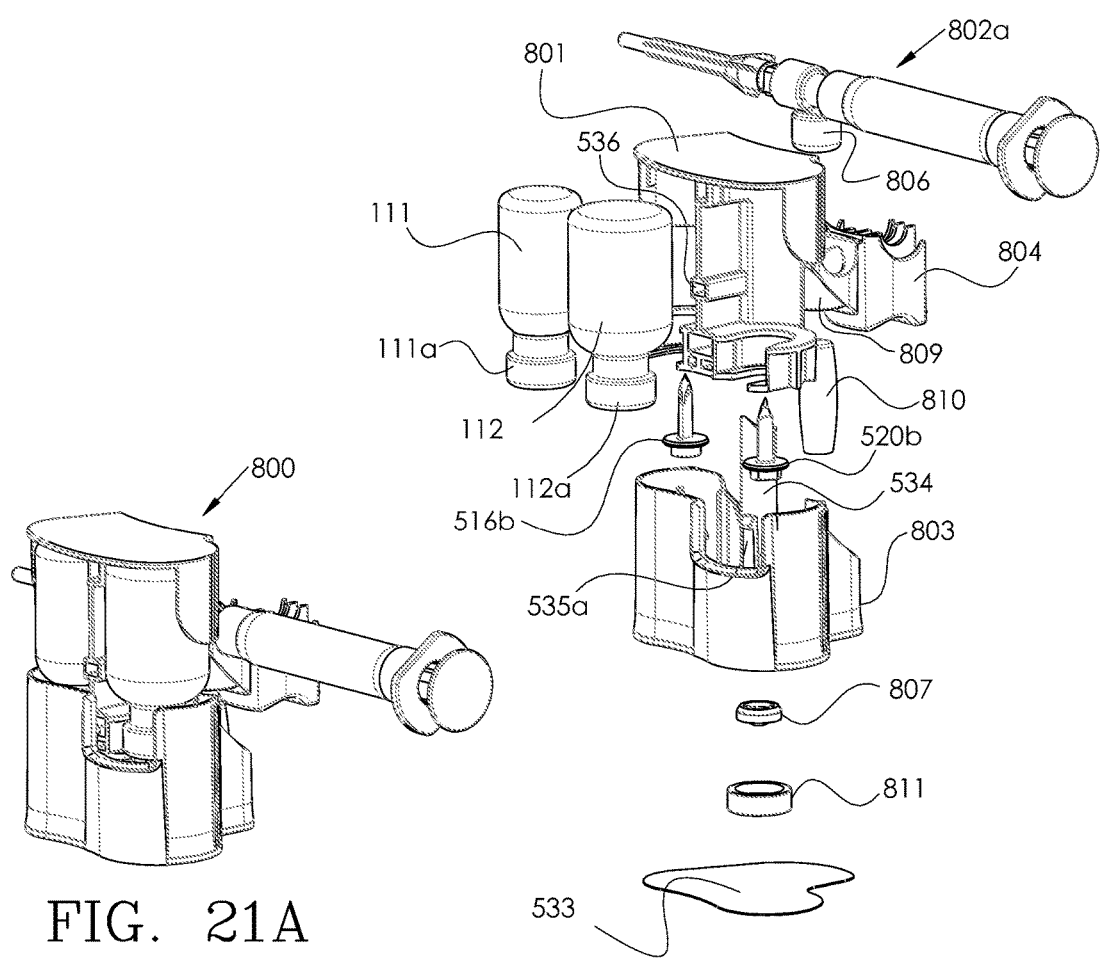
FIGS. 21A-21B are a perspective view and exploded view of an alternate embodiment of the fluid transfer and delivery device as disclosed and described herein.

FIG. 21A-21B are perspective and exploded views, respectively, of fluid transfer and delivery device 800 configured to receive a fluid delivery device that is received by device 800 in a horizontal configuration, as shown (wherein the longitudinal axis of fluid delivery device is essentially normal to the delivery device accessing means). In this configuration, activation of the device can be achieved with a delivery device having a needle (or cannula) and/or safety devices secured thereto, such as a needle & shield or needle/needle safety device. Device 800 comprises upper housing 801 slidably received by lower housing 803 as described above. Upper housing 801 is configured to accept horizontally oriented syringe 802a and adapter 806. Guide feature 534 in the lower housing 803 supports the upper housing. Locking features 535a in the lower housing are configured for interacting with corresponding catch features 536 on the upper housing to hold the components and housing sections together in the as-assembled and activated positions. Upon activation, spikes 516b, 520b pierce septums 111a, 112a of media containers 111, 112. Bypass syringe 802a is received by a hinged closure 804 connected to upper housing 801, for example, via a living hinge (not shown) or other means providing rotation (e.g., 2-piece designs). The internal cavity of syringe 802a is accessed via septum 805 (see FIG. 22B) in adapter 806. On the underside of lower housing 803 is located a cavity receiving check valve 807 and optional filter 811. Upon actuation of device 800, septum 805 of adapter is pierced by delivery device accessing member 808 (see FIG. 22B) projecting vertically from lower housing 803 and aligned with guide feature 809 of upper housing 801. Access member 808 is covered by elastomeric sleeve 810, which is configured to seal access member 808 in the un-activated state and compressed during device actuation to allow fluid communication through fluid conduit in access member 808. Sleeve 810 can maintain sterility of the device prior to first use and thereafter. Prior to device actuation, elastomeric sleeve 810 seals delivery device access member 808. Optional filter 811 is positioned in front of check valve 807 or between check valve 807 and conduit 521. Flat sheet or film component base plate 533 closes the molded channels to create the fluid conduits, that when overlaid with the lower housing 803, forms fluid conduits 517, 518, and 521 (not shown) creating the corresponding fluid conduits for spikes 516b, 520b and connection for syringe and vent conduit (not shown) similar to that previously disclosed in the third embodiment. Check valve 807 and septum 805 of syringe 802a are configured for creating a closed fluidic system when device 800 is activated.

Figure 22A:
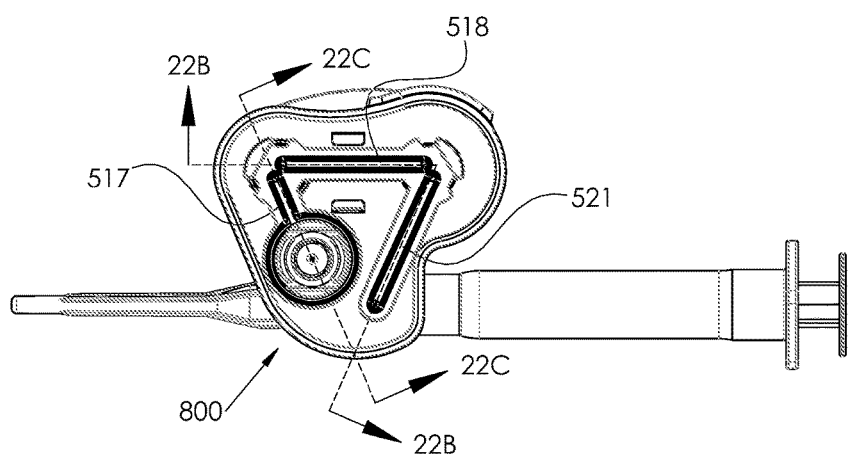
FIGS. 22A-22C are section plane and corresponding cross-sectional views of the fluid transfer and delivery device of FIG. 21A in an activated state.
Figures 22B, 22C:
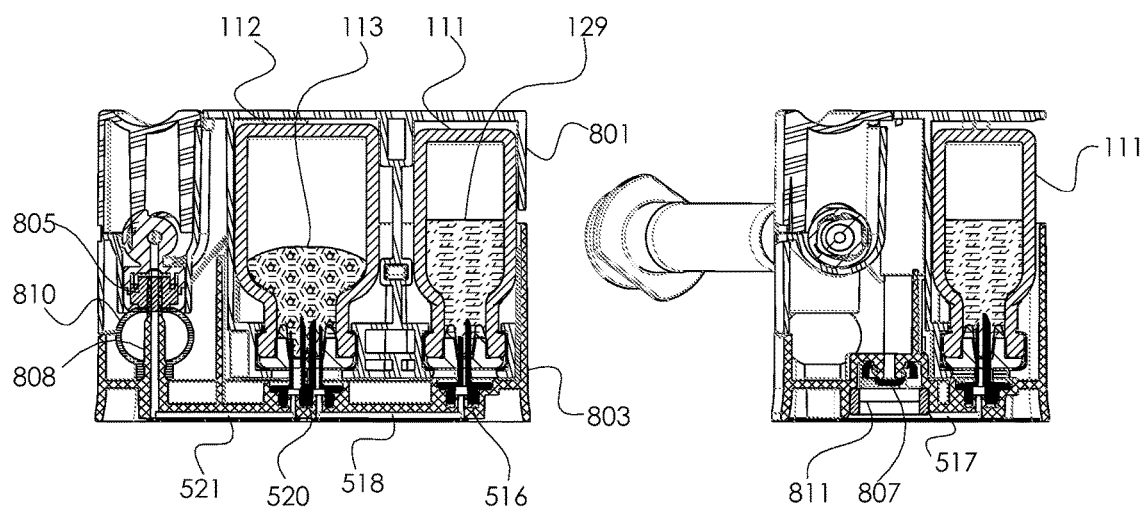
Figure 23A:
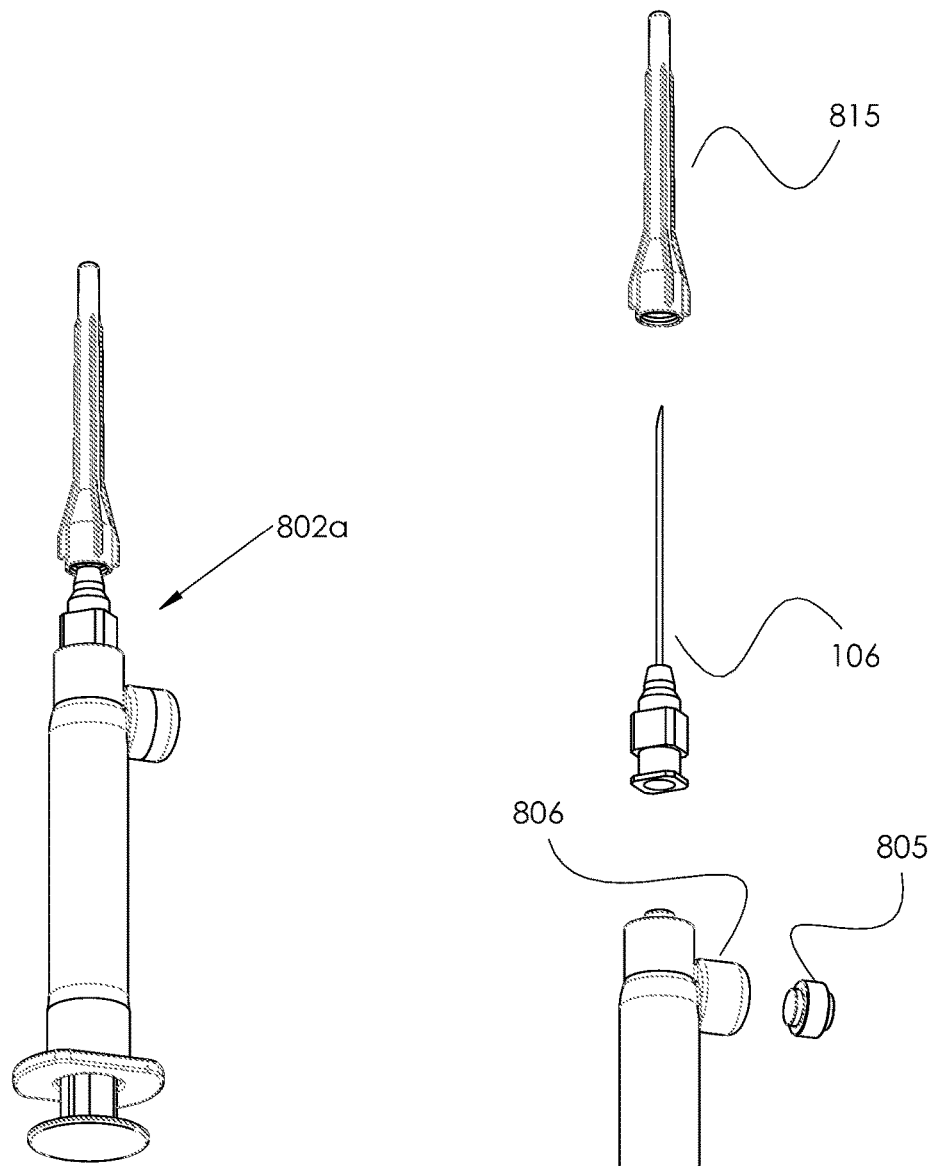
FIGS. 23A-23B are a perspective view and exploded view of a syringe with integral adapter as disclosed and described herein.
Figure 23B:
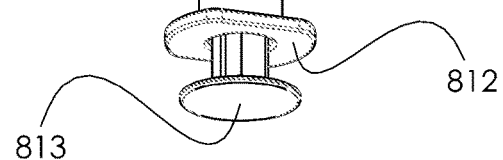

FIG. 22A-22C are section plane and corresponding cross-sectional views of transfer device 800 shown in an activated state, in a theoretical instance just before any fluid transfer has taken place, in combination with a standard syringe with adapter 816. Container access means 516 and 520 have sealably pierced their respective media containers 111 and 112 providing fluid communication between fluid conduit 518, first container 111 containing fluid 129, intermediate container 112 containing drug media 113 (e.g., under vacuum), second intermediate fluid conduit 521, adapter 806, and syringe 802b. Elastomeric sleeve 810 compresses/collapses, exposing accessing member 808 for penetrating elastomeric septum 805 of adapter 806 thus providing fluid communication of the syringe interior with the transfer system device. When media containers 111 and 112 are accessed via 516 and 520, respectively, check valve 807 opens allowing air into the system. Filter 811, located between check valve 807 and fluid conduit 517, prevents materials greater than a predetermined pore size from entering the system from the atmosphere and fluid from exiting the system.

Syringe Bypass Adapter

Figure 25A:
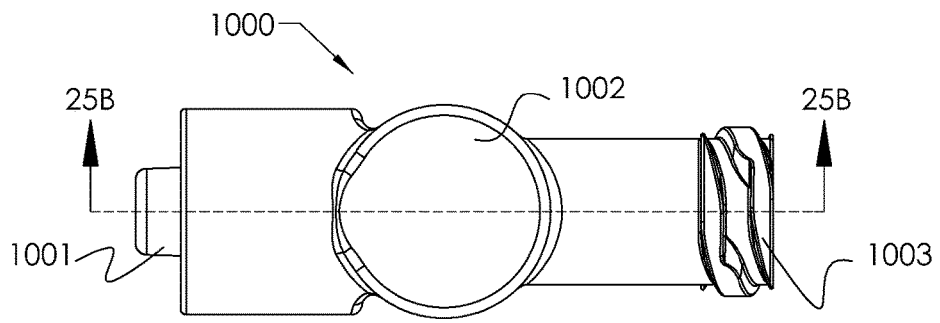
FIGS. 25A-25C are a top plan view and corresponding cross-sectional views of a first adapter embodiment as disclosed and described herein.

In one embodiment, an adapter is provided for coupling with a standard syringe for use with the transfer device 800. FIG. 25A depicts a side view of bypass adapter 1000 configured for use with a standard syringe in combination with the transfer device 800. Adapter 1000 comprises a male luer connector 1001 for attachment of a hypodermic needle hub, a female luer connector 1003 for attachment of a syringe, and a septum housing 1002 arranged between the connector ends. In one embodiment, the septum housing comprises a conduit perpendicular the connector axis.

Figure 25B:
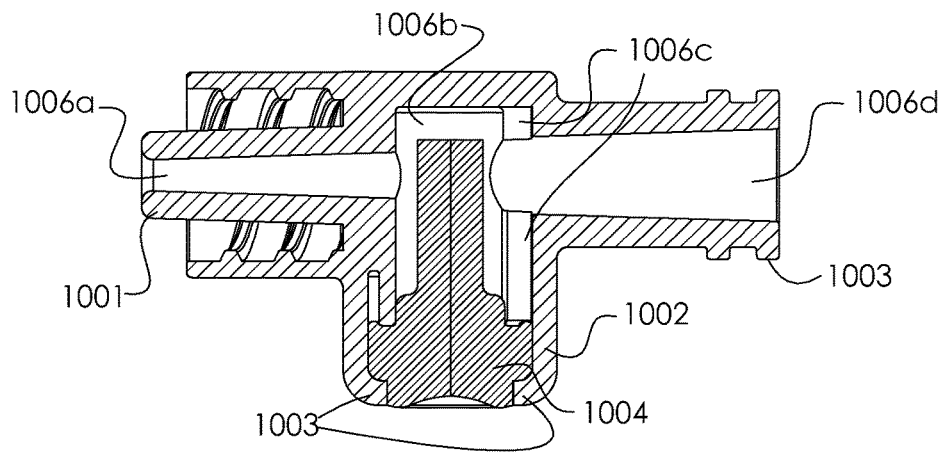

FIG. 25B depicts a section view of the bypass adapter of 25A prior to access by access member 808 of transfer device 800, showing septum 1004 for controlling fluid flow between the male luer lock connector 1001 and the female connector 1003 in the septum housing 1002. Spit-septum 1004 controls fluid path through adapter and housing, for example, conduit 1006a through male connector 1001, conduit 1006b and slot 1006c in fluid communication with conduit 1006d of female luer connector 1003. Housing 1002 and connectors 1001 and 1003 can fabricated as a solid unit with housing ends 1003 initially projecting parallel to each other so that septum 1004 can be introduced and connector 1003 rolled over to seal septum 1004 in housing.

Figure 25C:
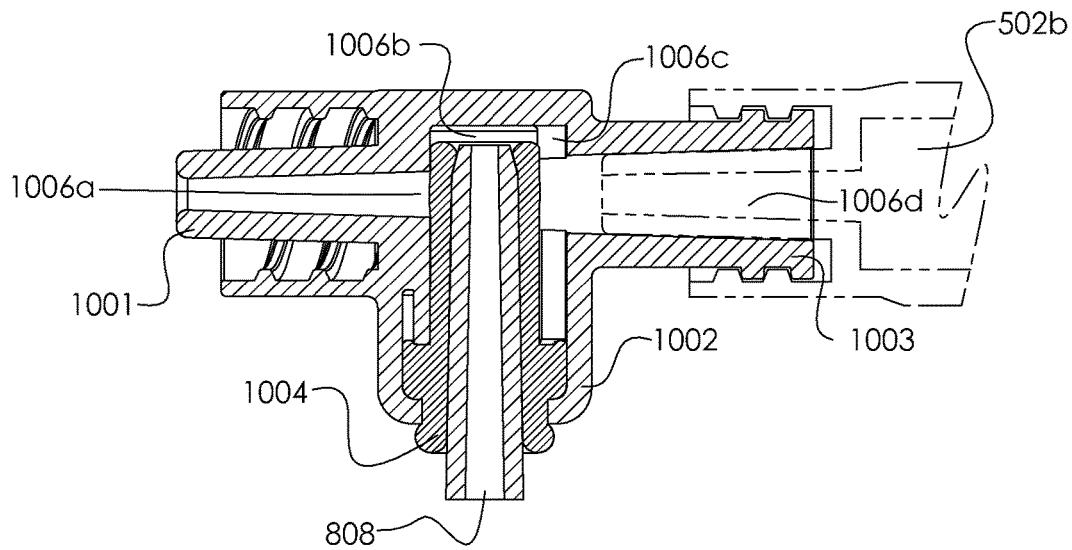

FIG. 25C depicts a section view of the bypass adapter 1000 in the activated position showing access member 808 of transfer device 800 penetrating elastomeric slit-septum 1004. Slit-septum 1004 has been displaced by the cannula such that the fluid path of the male connector 1006a is blocked while the fluid path of the female connector 1003 remains open due to slot 1006c in the septum housing 1002, providing a flow path from the transfer device to syringe 502b without fluid transfer to the cannula 106 of syringe 502b.

Figure 26A:
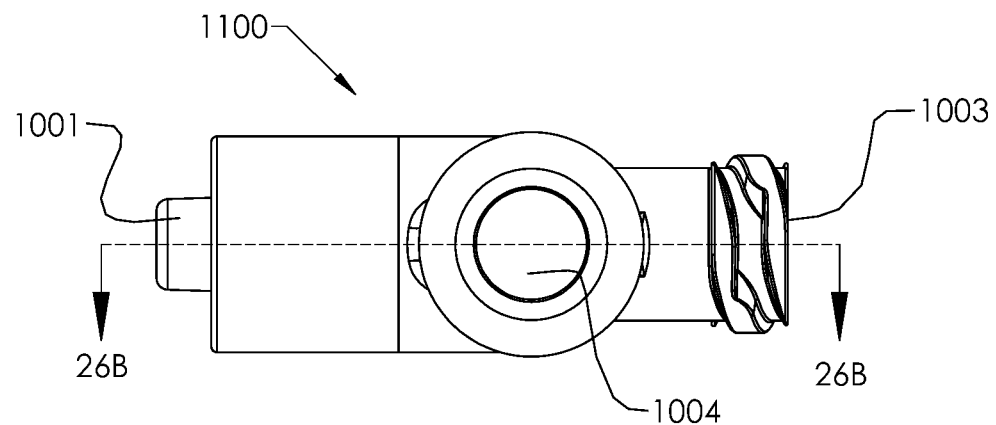
FIGS. 26A-26B are a top plan view and corresponding cross-sectional view of a second adapter embodiment as disclosed and described herein.

FIG. 26A depicts a side view of an alternate configuration of a bypass adapter, thus, adapter 1100 comprises male luer connector 1001 connector for attachment of a hypodermic needle hub, female luer connector 1003 for attachment of a syringe, and septum housing 1002 arranged between the connector ends. In one embodiment, septum housing 1102 comprises a conduit perpendicular the connector axis.

Figure 26B:
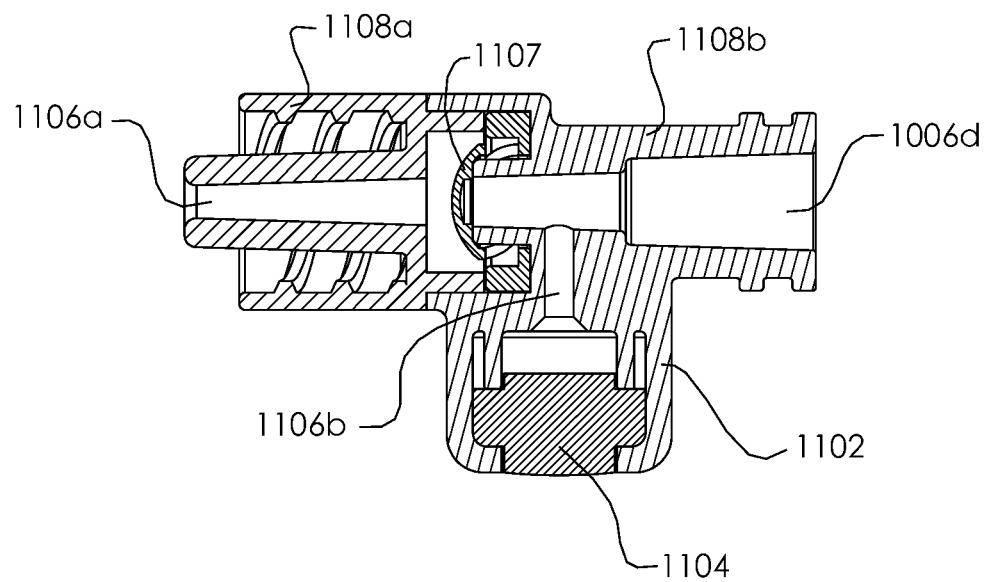

FIG. 26B depicts a section view of the bypass adapter of 26A showing elastomeric septum 1104 located between the male luer lock connector 1001 and the female connector 1003 in the septum housing 1102, creating a fluid flow path of conduits 1106a, 1106b, and 1106c, through male connector 1108a, septum housing 1102, and female connector 1108b, respectively. Housing 1102 and connector 1108b can be fabricated separately from connector 1108a. Housing ends 1003 initially projecting parallel to each other so that septum 1104 can be introduced and connector 1003 rolled over to seal septum 1104 in housing. In this configuration the male luer connector 1108a can be joined to connector 1008b and secure one-way valve 1107. Valve 1107 closes off the fluid path to male luer conduit 1106a when fluid is being transferred between septum fluid conduit 1106b and female luer fluid conduit 1106d.

Figure 27A:
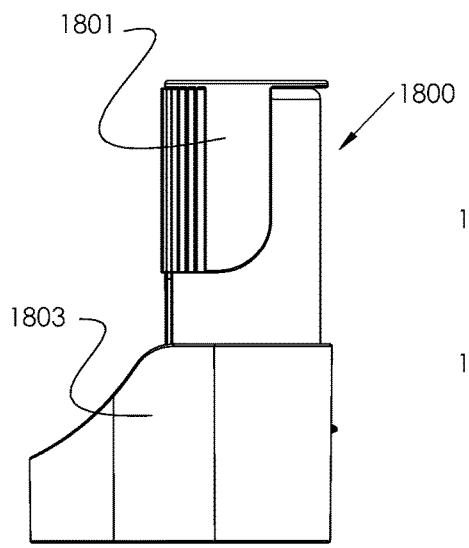
FIGS. 27A-27D are perspective views of a twelfth embodiment of a fluid transfer and delivery device, as disclosed and described herein.
Figure 27B:
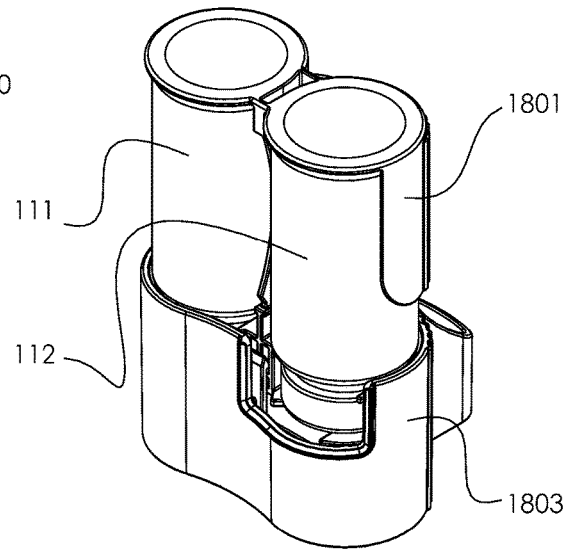
Figure 27C:
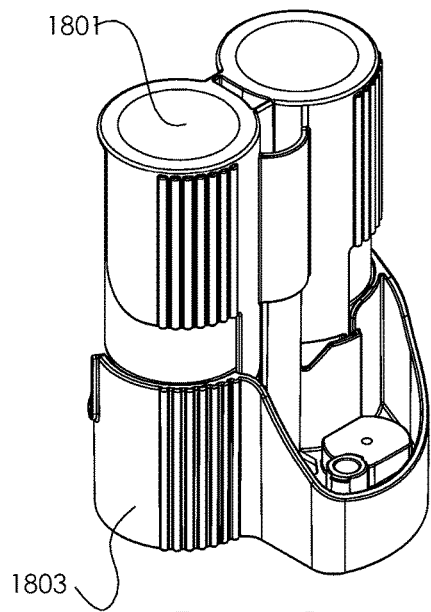
Figure 27D:
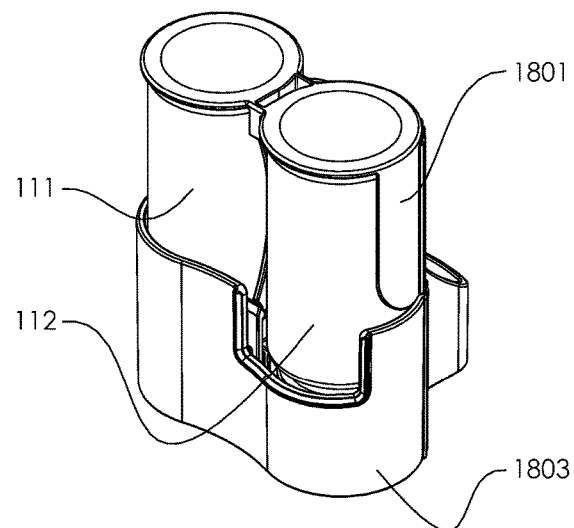

FIG. 27A depicts a side view of transfer device 1800 that is configured to accept two 10 mL vials 111 & 112 with 20 mm closures in a symmetrical upper housing 1801 supported in the lower housing 1803. FIGS. 27B and 27C are front and rear perspective views, respectively of device 1800 in the pre-activated state with vials positioned for mixing and transfer. FIG. 27D is a front perspective view of device 1800 in an activated state after housing 1801 is urged downward and slidably received by lower housing 1803.

Figure 28A:
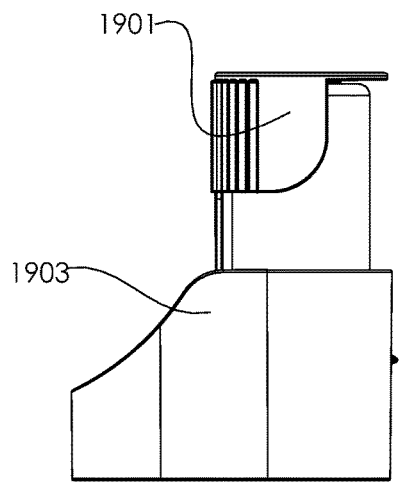
FIGS. 28A-28D are perspective views of a thirtieth embodiment of a fluid transfer and delivery device, as disclosed and described herein.
Figure 28B:
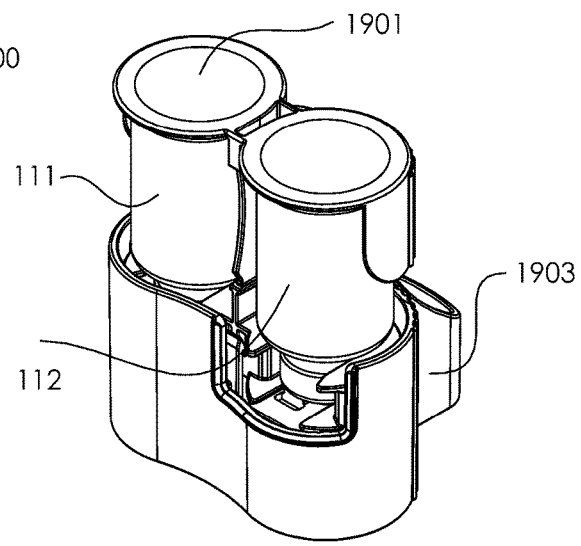
Figure 28C:
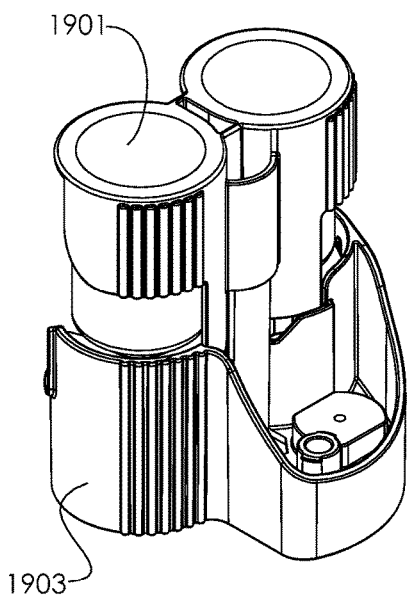
Figure 28D:
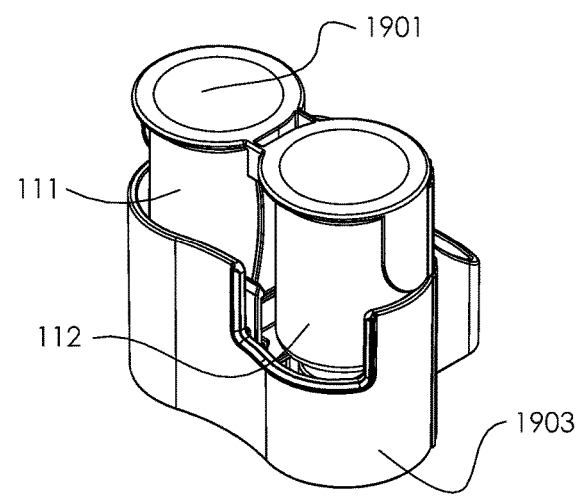

FIG. 28A depicts a side view of transfer device 1900 that is configured to accept two 5 mL vials 111 & 112 with 13 mm closures in a symmetrical upper housing 1901 supported in the lower housing 1903. FIGS. 28B and 28C are front and rear perspective views, respectively of device 1900 in the pre-activated state with vials positioned for mixing and transfer. FIG. 27D is a front perspective view of device 1900 in an activated state after frame 1901 is urged downward and slidably received by lower housing 1903.

Manufacturing

All of the components of the proposed embodiments may be injection molded with the exception of the syringe needle and drug vials. Alternate manufacturing methods for the elastomeric components may include compression or transfer molding. Design intent may be such that components are molded with simple open/close tooling to reduce tooling cost and cycle times. The fluid conduits as seen, for example in FIG. 5C, at callouts 117, 118, 121 may be formed by injection molding, where the conduits are channels formed in one plane in an "open-topped" configuration, and which are subsequently closed to create separate conduits by adhering a base plate comprised of a flat sheet or film of suitable material across the open-topped surface. The base plate may be laser welded, ultrasonically welded, heat sealed, solvent bonded, and the like to the lower housing by. The base plate may be die cut rather than injection molded as appropriate. Spikes 516b and 520b can be locked into cavities via many methods, including but not limited to press-fitting, ultrasonic welding, heat staking, and through the use of adhesives. Filter 811 can be locked into its respective cavity via many methods, including but not limited to press-fitting, ultrasonic welding, heat staking, and through the use of adhesives.

Component Coupling

Where feature definition may not be able to be achieved by single tool molding; ultrasonic welding, adhesives or mechanical retention may be employed to join components. Furthermore, where dissimilar materials may be advantageous, a 2-shot molding technique may be utilized, such as creating a non-slip surface to the bottom flange of the lower housing. The disclosed and described device provides multiple advantageous features, summarized below.

Reduced Procedural Steps

The device described herein may reduce the number of steps required to prepare a mixture. The combination of accessing multiple vials in a single stroke as well as having negatively pressurized media containers to compel the transfer of fluids rather than manual human interaction may prove to significantly reduce the steps required when compared to contemporary transfer devices of this kind.

Multiple Media Container Access Via External Force

The device described herein may allow for accessing multiple media containers when a single force is applied. The force required for this action may be mitigated by the increased ergonometric arrangement of the device. The inherent stability of multiple points of contact, a larger footprint and substantial guiding surfaces make the device significantly easier to operate.

Reduced Manufacturing Complexity

The device described herein uses standard drug vials as opposed to prefilled syringes. Often prefilled syringe systems are assumed to reduce the number of steps and/or simplify the preparation and administration process. The device described here eliminates the need to attach the prefilled syringe plunger and the need to inject the diluent into the drug vial. This reduces steps over comparable prefilled syringe systems and is more compact, allowing for saved space in clinical and home environments and its inclusion in automated pharmacy systems. The device eliminates the complexity of validation and filling of as compared to prefills, allows for full flexibility of varying the volume of drug vial, and utilizes existing processes and stability data readily available by filling standard drug vials. This results in lower costs as well in most cases. Also, by eliminating pre-filled syringes, the syringe herein may be more readily customized for the specific application, employing features like passive needle safety, or other fittings such as spray nozzles, varying needle types, valved male luers, or capped slip or locking style luers. The syringe volume can be readily varied, and since the drug is contained for short durations within, there are fewer limitations with regards to gas or moisture barrier properties, extractables, leachables, or other drug compatibilities.

We claim:

1. A transfer device comprising:
a base plate without openings;
an upper housing; and
a lower housing securable to the base plate and providing multiple compartments, the lower housing slidably receiving a portion of the upper housing;
a fluidic conduit system integral with the lower housing providing fluid communication between the multiple compartments, the fluidic conduit system comprising:
(i) a first container accessing member having a longitudinal axis distally projecting essentially vertical from the lower housing, and having corresponding therewith a first fluid lumen and a second fluid lumen essentially parallel with the longitudinal axis, the first fluid lumen of the first container accessing member in fluid communication with a vent;
(ii) a second container accessing member having a longitudinal axis distally projecting essentially vertical from the lower housing, and having corresponding therewith a first fluid lumen and a second fluid lumen essentially parallel with the longitudinal axis, the first fluid lumen of the second container accessing member in fluid communication with the second fluid lumen of the first container accessing member; and
(iii) a delivery device accessing member configured to control fluid communication between a delivery device and the fluidic conduit system, the delivery device accessing member having a first fluid lumen in fluid communication with the second fluid lumen of the second container accessing member, wherein the delivery device accessing member is configured with at least one of the following: (a) a valved access connector; and (b) a cannula in combination with a collapsible elastomeric sleeve;
wherein the lower housing comprises:
(i) a first flow channel fluidically communicating the first fluid lumen of the first container accessing member with at least one of the vent or a check valve;
(ii) a second flow channel fluidically communicating the first fluid lumen of the second container accessing member with the second fluid lumen of the first container accessing member, and
(iii) a third flow channel fluidically communicating the first fluid lumen of the delivery device accessing member with the second fluid lumen of the second container accessing member;
the flow channels (i)-(iii) forming the fluidic conduit system by a combination of the base plate and the lower housing are physically isolated from each other.

2. The transfer device of claim 1, further comprising a check valve in fluid communication with the first flow channel.

3. The transfer device of claim 1, wherein the valved access connector is a female valved connector and the collapsible elastomeric sleeve have a first state fluidically sealing the first fluid lumen of the delivery device access member, and a second state providing fluid communication between a delivery device and the fluidic conduit system.

4. The device of claim 3, further comprising a syringe configured to operably couple with the delivery device accessing member.

5. The device of claim 4, wherein the syringe comprises a distal end having a male valved connector having a first state fluidically sealing the distal end of the syringe, and a second state operably coupled to the delivery device accessing member so as to provide fluid communication between the syringe and the fluidic conduit system.

6. The device of claim 4, wherein the syringe comprises a distal end having a male valved connector having a first state fluidically sealing the distal end of the syringe, and a second state operably coupled to the delivery device accessing member comprising the female valved connector.

7. A method of mixing and transferring, the method comprising:
providing a device as defined in claim 1; and
optionally, providing at least one container having a pierceable opening.

8. The method of claim 7, further comprising:
introducing at least two containers to the device such that the pierceable openings are operably configured with the first or the second container accessing member; and
sequentially or concurrently, operably coupling a syringe to the delivery device accessing member.

9. The method of claim 8, further comprising urging the upper housing towards the lower housing so that the at least two containers are accessed by the first or the second container accessing member through the pierceable openings.

10. The method of claim 8, further comprising, sequentially or concurrently, mixing and transferring at least a portion of the contents from the at least one container to the device.

11. A transfer device comprising:
an upper housing; and
a lower housing slidably receiving a portion of the upper housing; the lower housing comprising:
(i) a first container accessing member having corresponding therewith a first fluid lumen and a second fluid lumen, the first fluid lumen of the first container accessing member in fluid communication with a vent or a check valve;
(ii) a second container accessing member having corresponding therewith a first fluid lumen and a second fluid lumen, the first fluid lumen of the second container accessing member in fluid communication with the second fluid lumen of the first container accessing member; and
(iii) a delivery device accessing member having a first fluid lumen in fluid communication with the second fluid lumen of the second container accessing member, the delivery device accessing member being adjacent the vent or the check valve;
(iv) a first flow channel fluidically communicating the first fluid lumen of the first container accessing member with the vent or the check valve;
(v) a second flow channel fluidically communicating the first fluid lumen of the second container accessing member with the second fluid lumen of the first container accessing member, and
(vi) a third flow channel fluidically communicating the first fluid lumen of the delivery device accessing member with the second fluid lumen of the second container accessing member;

wherein the lower housing is in a sealed relationship with a base plate devoid of openings.

* * * * *